(12) United States Patent
Kawana et al.

(10) Patent No.: US 11,173,100 B2
(45) Date of Patent: Nov. 16, 2021

(54) MULTI-PART DENTAL CEMENT

(71) Applicant: KURARAY NORITAKE DENTAL INC., Kurashiki (JP)

(72) Inventors: Mariko Kawana, Niigata (JP); Shumei Ishihara, Okayama (JP); Mitsuru Takei, Frankfurt (DE); Kengo Futami, Tokyo (JP)

(73) Assignee: KURARAY NORITAKE DENTAL INC., Kurashiki (JP)

( * ) Notice: Subject to any disclaimer, the term of this patent is extended or adjusted under 35 U.S.C. 154(b) by 38 days.

(21) Appl. No.: 16/343,853

(22) PCT Filed: Oct. 20, 2017

(86) PCT No.: PCT/JP2017/038063
§ 371 (c)(1),
(2) Date: Apr. 22, 2019

(87) PCT Pub. No.: WO2018/074600
PCT Pub. Date: Apr. 26, 2018

(65) Prior Publication Data
US 2019/0262240 A1    Aug. 29, 2019

(30) Foreign Application Priority Data
Oct. 21, 2016    (JP) .............................. JP2016-207175

(51) Int. Cl.
*A61K 6/887*    (2020.01)
*A61K 6/76*    (2020.01)
(52) U.S. Cl.
CPC ................ *A61K 6/887* (2020.01); *A61K 6/76* (2020.01)
(58) Field of Classification Search
CPC .................................................... A61K 6/887
See application file for complete search history.

(56) References Cited

U.S. PATENT DOCUMENTS 6,762,242 B1    7/2004    Torto et al.
2003/0181541 A1    9/2003    Wu et al.
(Continued)

FOREIGN PATENT DOCUMENTS

JP    2002-255721 A    9/2002
JP    2002-541309 A    12/2002
(Continued)

OTHER PUBLICATIONS

English machine translation of JP-2011213514-A.*
(Continued)

*Primary Examiner* — Michael F Pepitone
(74) *Attorney, Agent, or Firm* — Oblon, McClelland, Maier & Neustadt, L.L.P.

(57) ABSTRACT

The present invention provides a dental cement showing excellent storage stability, undergoing little change in paste properties during long-term storage, and having a small solidification risk during long-term storage. The present invention relates to a multi-part dental cement comprising: a first paste comprising an acid group-containing (meth) acrylic polymerizable monomer (a), a polyfunctional (meth) acrylic polymerizable monomer (b) containing no acid group, an oxidizing agent (c-1) of a chemical polymerization initiator, and a filler (d); and a second paste comprising a polyfunctional (meth)acrylic polymerizable monomer (b) containing no acid group, a reducing agent (c-2) of a chemical polymerization initiator, and a filler (e), wherein the filler (d) is treated with a surface treatment agent and has an average particle diameter of 0.01 to 50.0 μm, the surface treatment agent comprises a silane coupling agent (A) represented by the general formula (1) and an organosilazane (B) represented by the general formula (2).

16 Claims, 1 Drawing Sheet

(56) References Cited

U.S. PATENT DOCUMENTS

| | | | |
|---|---|---|---|
| 2005/0009946 A1 | | 1/2005 | Oguri et al. |
| 2010/0267856 A1* | | 10/2010 | Shinoda .................. A61K 6/887 |
| | | | 522/11 |
| 2012/0016094 A1* | | 1/2012 | Takei ..................... A61K 6/887 |
| | | | 526/181 |
| 2012/0202913 A1* | | 8/2012 | Kawana .................. A61K 6/54 |
| | | | 522/84 |
| 2015/0320646 A1 | | 11/2015 | Kameya et al. |

FOREIGN PATENT DOCUMENTS

| | | | | |
|---|---|---|---|---|
| JP | 2003-96122 | A | | 4/2003 |
| JP | 2005-517688 | A | | 6/2005 |
| JP | 2009-292761 | A | | 12/2009 |
| JP | 2011-16775 | A | | 1/2011 |
| JP | 2011-213514 | A | | 10/2011 |
| JP | 2011213514 | A | * | 10/2011 |
| JP | 2011-225526 | A | | 11/2011 |
| WO | WO 03/063804 | A1 | | 8/2003 |
| WO | WO 2014/083842 | A1 | | 6/2014 |
| WO | WO 2015/190100 | A1 | | 12/2015 |

OTHER PUBLICATIONS

Extended European Search Report dated May 12, 2020 in European Patent Application No. 17862133.0, 9 pages.
International Search Report dated Dec. 12, 2017 in PCT/JP2017/038063 filed on Oct. 20, 2017.

* cited by examiner

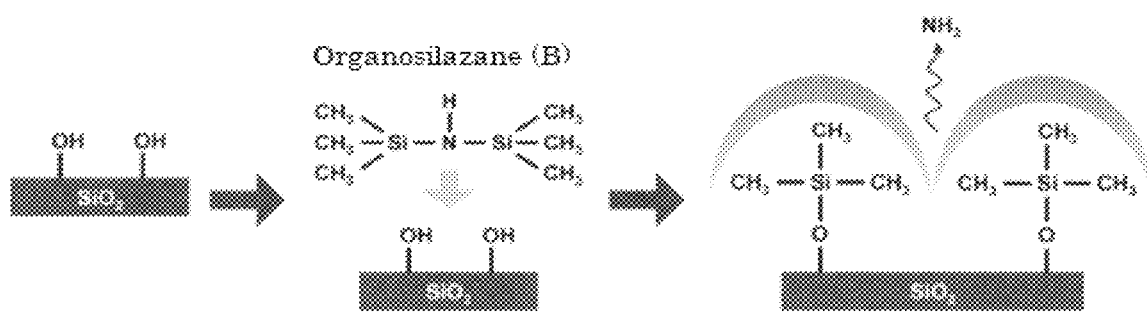

MULTI-PART DENTAL CEMENT

TECHNICAL FIELD

The present invention relates to a multi-part dental cement used, for example, for luting dental prostheses such as crowns, inlays, and bridges to tooth structures during dental treatment. More specifically, the present invention relates to a multi-part dental cement having excellent storage stability, undergoing little Change in paste properties during long-term storage, and having a small solidification risk in a long-term perspective.

CROSS REFERENCE TO RELATED APPLICATIONS

This application is a national stage patent application of international patent application PCT/P2017/038063, filed on Oct. 20, 2017, the text of which is incorporated by reference, and claims foreign priority to Japanese Patent Application No. 2016-207175, filed on Oct. 21, 2016, the entire content of which is incorporated herein by reference.

BACKGROUND ART

For restorative treatment of tooth structures (enamel, dentin, and cementum) damaged, for example, by dental caries, dental cements are used as materials for luting dental prostheses such as crowns, inlays, and bridges to broken or chipped tooth crowns. Dental cements are usually paste-like, radical polymerization curable compositions composed of a polymerizable monomer, filler, and polymerization initiator.

(Meth)acrylates are generally used as polymerizable monomers contained in dental cements. A polymerizable monomer having an acid group such as a phosphate or carboxy group is contained to impart to dental cements self-adhesion to tooth structures and dental prostheses.

A component (for example, oxides, carbonates, and hydroxides of alkaline-earth metals, such as calcium, magnesium, and strontium, and acid-reactive fluoroaluminosilicate glass) commonly used in radical polymerization curable dental compositions is known to be disadvantageous as a filler of a self-adhesive dental composition containing a polymerizable monomer having an acid group, because in self-adhesive dental compositions, such a filler causes an acid-base reaction, neutralization, salt formation, or a chelation reaction with the polymerizable monomer having an acid group to impair the adhesiveness of the self-adhesive dental compositions or change the paste properties.

Patent Literature 1 discloses a self-adhesive dental cement composition containing a silica filler treated with a silane coupling agent poorly reactive with an acid component.

CITATION LIST

Patent Literature

Patent Literature 1: JP 2009-292761 A

SUMMARY OF INVENTION

Technical Problem

When, for example, the silica filler described in Patent Literature 1 and being poorly reactive with an acid component is used, a reaction between the filler and acid component is suppressed; however, while stored, the resultant self-adhesive dental cement containing a polymerizable monomer having an acid group may undergo a large change in paste properties or may be solidified. It is therefore an object of the present invention to provide a dental cement showing excellent storage stability, undergoing little change in paste properties during long-term storage, and having a small solidification risk during long-term storage.

Solution to Problem

That is, the present disclosure provides the following inventions.

[1] A multi-part dental cement comprising a first paste and a second paste, wherein the first paste comprises an acid group-containing (meth) acrylic polymerizable monomer (a), a polyfunctional (meth) acrylic polymerizable monomer (b) containing no acid group, an oxidizing agent (c-1) of a chemical polymerization initiator, and a filler (d), the second paste comprises a polyfunctional (meth)acrylic polymerizable monomer (b) containing no acid group, a reducing agent (c-2) of a chemical polymerization initiator, and a filler (e), the filler (d) is treated with a surface treatment agent and has an average particle diameter of 0.01 to 50.0 μm, the surface treatment agent comprises a silane coupling agent (A) represented by the following general formula (1):

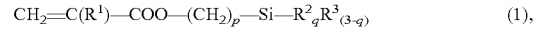

$$CH_2=C(R^1)-COO-(CH_2)_p-Si-R^2_q R^3_{(3-q)} \quad (1),$$

wherein $R^1$ is a hydrogen atom or a methyl group, $R^2$ is an optionally substituted hydrolyzable group, $R^3$ is an optionally substituted $C_1$ to $C_3$ alkyl group, p is an integer of 1 to 13, and q is 2 or 3, and an organosilazane (B) represented by the following general formula (2):

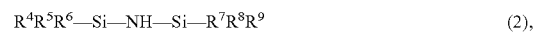

$$R^4 R^5 R^6-Si-NH-Si-R^7 R^8 R^9 \quad (2),$$

wherein $R^4$, $R^5$, and $R^6$ are each independently a hydrogen atom or an optionally substituted $C_1$ to $C_3$ alkyl group, at least one of $R^4$, $R^5$, and $R^6$ is an optionally substituted $C_1$ to $C_3$ alkyl group, $R^7$, $R^8$, and $R^9$ are each independently a hydrogen atom or an optionally substituted $C_1$ to $C_3$ alkyl group, and at least one of $R^7$, $R^8$, and $R^9$ is an optionally substituted $C_1$ to $C_3$ alkyl group.

[2] The multi-part dental cement according to [1], wherein the filler (e) is at least not surface-treated with the organosilazane (B).

[3] The multi-part dental cement according to [1], wherein the filler (e) is surface-treated at least with the organosilazane (B).

[4] The multi-part dental cement according to any one of [1] to [3], wherein $R^2$ is an unsubstituted hydrolyzable group, $R^3$ is an unsubstituted $C_1$ to $C_3$ alkyl group, $R^4$, $R^5$, and $R^6$ are each independently a hydrogen atom or an unsubstituted $C_1$ to $C_3$ alkyl group, at least one of $R^4$, $R^5$, and $R^6$ is an unsubstituted $C_1$ to $C_3$ alkyl group, $R^7$, $R^8$, and $R^9$ are each independently a hydrogen atom or an unsubstituted $C_1$ to $C_3$ alkyl group, and at least one of $R^7$, $R^8$, and $R^9$ is an unsubstituted $C_1$ to $C_3$ alkyl group.

[5] The multi-part dental cement according to any one of [1] to [4], wherein $R^2$ is an unsubstituted linear or branched $C_1$ to $C_6$ alkoxy group.

[6] The multi-part dental cement according to any one of [1] to [5], wherein W is a methyl group.

[7] The multi-part dental cement according to any one of [1] to [6], wherein p is 2 to 10.

[8] The multi-part dental cement according to any one of [1] to [7], wherein q is 3.

[9] The multi-part dental cement according to any one of [1] to [8], wherein the silane coupling agent (A) is at least one selected from the group consisting of 2-methacryloyloxyethyltrimethoxysilane, 3-methacryloyloxypropyltrimethoxysilane, 4-methacryloyloxybutyltrimethoxysilane, 5-methacryloyloxypentyltrimethoxysilane, and 6-methacryloyloxyhexyltrimethoxysilane.

[10] The multi-part dental cement according to any one of [1] to [9], wherein the organosilazane (B) is at least one selected from the group consisting of 1,1,3,3-tetramethyldisilazane, 1,1,1,3,3,3-hexamethyldisilazane, and 1,1,1,3,3-pentamethyldisilazane.

[11] The multi-part dental cement according to any one of [1] to [10], wherein the molar ratio between the silane coupling agent (A) and the organosilazane (B) is [silane coupling agent (A)]:[organosilazane (B)]=1:1 to 1:20.

[12] The multi-part dental cement according to any one of [1] to [11], wherein
in the first paste, the content of the acid group-containing (meth)acrylic polymerizable monomer (a) is 1 to 50 parts by mass in 100 parts by mass of the total polymerizable monomer components and the content of the filler (d) is 1 to 200 parts by mass with respect to 100 parts by mass of the total polymerizable monomer components, and
in a mixture of the first paste and the second paste, the content of a polyfunctional (meth)acrylic polymerizable monomer (b) containing no acid group is 30 to 95 parts by mass in 100 parts by mass of the total polymerizable monomer components.

[13] The multi-part dental cement according to any one of [1] to [12], wherein at least one of the first paste and the second paste further comprises a photopolymerization initiator (f).

[14] The multi-part dental cement according to any one of [1] to [13], wherein at least one of the first paste and the second paste further comprises an amide proton-containing polyfunctional (meth)acrylamide polymerizable monomer (h).

[15] The multi-part dental cement according to [14], wherein the content of the amide proton-containing polyfunctional (meth)acrylamide polymerizable monomer (h) is 0.1 to 30 parts by mass in 100 parts by mass of the total polymerizable monomer components.

[16] The multi-part dental cement according to any one of [1] to [15], wherein at least one of the first paste and the second paste further comprises a hydrophilic monofunctional polymerizable monomer (i).

[17] The multi-part dental cement according to [16], wherein the hydrophilic monofunctional polymerizable monomer (i) is at least one selected from the group consisting of a hydrophilic monofunctional (meth)acrylate polymerizable monomer and a hydrophilic monofunctional (meth)acrylamide polymerizable monomer.

[18] The multi-part dental cement according to any one of [1] to [17], wherein at least one of the first paste and the second paste further comprises a polymerization accelerator (g).

Advantageous Effects of Invention

The present invention provides a dental cement showing excellent storage stability, undergoing little change in paste properties during long-term storage, and having a small solidification risk during long-term storage.

BRIEF DESCRIPTION OF DRAWING

FIG. 1 illustrates a reaction mechanism in which an organosilazane (B) according to an embodiment of the present invention is 1,1,1,3,3,3-hexamethyldisilazane.

DESCRIPTION OF EMBODIMENTS

A multi-part dental cement of the present invention comprises a first paste and a second paste, wherein
the first paste comprises an acid group-containing (meth) acrylic polymerizable monomer (a), a polyfunctional (meth) acrylic polymerizable monomer (b) containing no acid group, an oxidizing agent (c-1) of a chemical polymerization initiator, and a filler (d),
the second paste comprises a polyfunctional (meth)acrylic polymerizable monomer (b) containing no acid group, a reducing agent (c-2) of a chemical polymerization initiator, and a filler (e),
the filler (d) is treated with a surface treatment agent and has an average particle diameter of 0.01 to 50.0 μm,
the surface treatment agent comprises a silane coupling agent (A) represented by the following general formula (1):

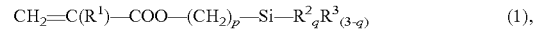

$$CH_2=C(R^1)-COO-(CH_2)_p-Si-R^2_q R^3_{(3-q)} \quad (1),$$

wherein $R^1$ is a hydrogen atom or a methyl group, $R^2$ is an optionally substituted hydrolyzable group, $R^3$ is an optionally substituted $C_1$ to $C_3$ alkyl group, p is an integer of 1 to 13, and q is 2 or 3, and
an organosilazane (B) represented by the following general formula (2):

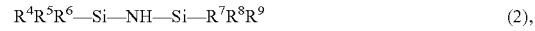

$$R^4 R^5 R^6-Si-NH-Si-R^7 R^8 R^9 \quad (2),$$

wherein $R^4$, $R^5$, and $R^6$ are each independently a hydrogen atom or an optionally substituted $C_1$ to $C_3$ alkyl group, at least one of $R^4$, $R^5$, and $R^6$ is an optionally substituted $C_1$ to $C_3$ alkyl group, $R^7$, $R^8$, and $R^9$ are each independently a hydrogen atom or an optionally substituted $C_1$ to $C_3$ alkyl group, and at least one of $R^7$, $R^8$, and $R^9$ is an optionally substituted $C_1$ to $C_3$ alkyl group.

In the present specification, the upper limits and lower limits of value ranges (ranges of, for example, the contents of components, values calculated for components, values of physical properties, and values of symbols in formulae) can be combined appropriately.

It is not known exactly why the multi-part dental cement of the present invention has excellent storage stability, undergoes little change in paste properties during long-term storage, and has no solidification risk during long-term storage. The reasons are probably as follows. That is, the filler (d) has on its surface a functional group represented by $-(CH_2)_p-OOC-C(R^1)=CH_2$ ($R^4$ is a hydrogen atom or methyl group, and p is an integer of 1 to 13) and derived from a surface treatment with the silane coupling agent (A) and a $C_1$ to $C_3$ alkyl group derived from a surface treatment with the organosilazane (B). The filler (d) has $-(CH_2)_p-OOC-C(R^1)=CH_2$ on its surface. $-(CH_2)_p-OOC-C(R^1)=CH_2$ is imparted by a dehydration polycondensation reaction between silanol groups using the silane coupling agent (A) having a polymerizable group, and the $C_1$ to $C_3$ alkyl group is imparted by a deammoniation reaction involving the organosilazane (B). In a common treatment known as a conventional technique and using a silane coupling agent (A) alone, a silanol group (—SiOH) yielded by hydrolysis of an alkoxy group of the silane coupling agent (A) and a silanol group (—SiOH) on the surface of a filler (d) are chemically bonded by dehydration polycondensation. This allows the silanol group (—SiOH) on the surface of the filler (d) or silanol group (—SiOH) derived from the silane coupling agent (A) to remain as an unreacted product (hereinafter, such a remaining silanol group will be referred to as "remaining silanol group"). In the present invention, as shown in FIG. 1, the deammoniation reaction between the remaining silanol group (—SiOH) on the surface of the filler (d) or remaining silanol group (—SiOH) derived from the silane coupling agent (A) and the organosilazane (B) can make the remaining silanol group (—SiOH) hydrophobic. It can be thought that this treatment (deammoniation reaction) with the organosilazane (B) can reduce the remaining silanol group (—SiOH) on the surface of the filler (d) or remaining silanol group (—SiOH) derived from the silane coupling agent (A) to a minimum. Therefore, it is less likely that in one paste, a proton ($H^+$) yielded from the acid group-containing (meth)acrylic polymerizable monomer (a) which is an essential component for imparting adhesion to the multi-part dental cement, a hydroxy group (—OH) contained in another polymerizable monomer, or the like causes a strong interaction with the silanol group (—SiOH) due to hydrogen bonding. This is presumably the reason why the paste properties are stable during long-term storage and the solidification risk is very low.

Presumably for the above reasons, the multi-part dental cement comprising the filler (d) undergoes little change in paste properties, and has a small solidification risk during long-term storage.

First, the filler (d) used in the first paste of the multi-part dental cement of the present invention will be described.

The filler (d) has —$(CH_2)_1$—OOC—$C(R^1)$=$CH_2$ and the $C_1$ to $C_3$ alkyl group on its surface. $C_1$ to $C_3$ alkyl groups are repulsive to each other due to their hydrophobicity. Therefore, the filler (d) of the present invention is less likely to aggregate in the dental cement owing to the repulsion between $C_1$ to $C_3$ alkyl groups, and is also less likely to aggregate when in powder form.

As the filler (d), any known filler used in radical polymerization curable compositions for dental use can be used without any limitation as long as the filler (d) is treated with a surface treatment agent and has an average particle diameter of 0.01 to 50.0 μm, and the surface treatment agent comprises the silane coupling agent (A) represented by the formula (1) and the organosilazane (B) represented by the formula (2). Examples of the filler (d) include: various types of glasses [containing silica as a main component and optionally containing oxides of heavy metals, boron, aluminum, etc., for example: glass powders having typical compositions, such as fused silica, quartz, soda lime silica glass, E-glass, C-glass, borosilicate glass (Pyrex (registered trademark) glass); and glass powders for dental use, such as barium glass (GM 27884 and 8235 manufactured by Schott, and E-2000 and E-3000 manufactured by Esstech, Inc.), strontium borosilicate glass (E-4000 manufactured by Esstech, Inc.), lanthanum glass ceramics (GM 31684 manufactured by Schott), and fluoroaluminosilicate glass (GM 35429, G018-091, and G018-117 manufactured by Schott)]; various types of ceramics; composite oxides such as silica-titania and silica-zirconia; diatomaceous earth; kaolin; clay minerals (such as montmorillonite); activated white clay; synthetic zeolite; mica; calcium fluoride; ytterbium fluoride; yttrium fluoride; calcium fluoride having the surface coated with silica and having a core-shell structure; ytterbium fluoride having the surface coated with silica and having a core-shell structure; yttrium fluoride having the surface coated with silica and having a core-shell structure; calcium phosphate; barium sulfate; zirconium dioxide; titanium dioxide; hydroxyapatite; calcium phosphate having the surface coated with silica and having a core-shell structure; barium sulfate having the surface coated with silica and having a core-shell structure; zirconium dioxide having the surface coated with silica and having a core-shell structure; titanium dioxide having the surface coated with silica and having a core-shell structure; and hydroxyapatite having the surface coated with silica and having a core-shell structure. Among these, the various types of glasses, composite oxides such as silica-titania and silica-zirconia, calcium fluoride having the surface coated with silica and having a core-shell structure, ytterbium fluoride having the surface coated with silica and having a core-shell structure, yttrium fluoride having the surface coated with silica and having a core-shell structure, calcium phosphate having the surface coated with silica and having a core-shell structure, barium sulfate having the surface coated with silica and having a core-shell structure, zirconium dioxide having the surface coated with silica and having a core-shell structure, titanium dioxide having the surface coated with silica and having a core-shell structure, hydroxyapatite having the surface coated with silica and having a core-shell structure, ytterbium fluoride having the surface coated with silica and having a core-shell structure, and yttrium fluoride having the surface coated with silica and having a core-shell structure are suitable because, in that case, the filler (d) can be efficiently reacted with the silane coupling agent (A) or organosilazane (B). One of these may be used alone, or two or more thereof may be used in combination.

The average particle diameter of the filler (d) is 0.01 to 50.0 μm, preferably 0.03 to 20.0 μm, and more preferably 0.05 to 10.0 μm. When the average particle diameter of the filler (d) is within these ranges, sufficient mechanical strength can be obtained, and the paste does not become sticky and thus has good handling properties. In addition, the resultant cured product has high surface smoothness and gloss after polishing or good retention of the smoothness and gloss. In the present specification, the average particle diameter of the filler means the average particle diameter (average primary particle diameter) of the primary particles of the filler.

The average particle diameter of the filler (d) can be determined by particle size distribution analysis or electron microscopic observation. When the average particle diameter is 1.0 μm or more, a particle size distribution analyzer is preferably employed. When the average particle diameter is less than 1.0 μm, electron microscopic observation is preferably employed. To be more specific about the particle size distribution analysis, for example, the average particle diameter can be measured using a 0.2% aqueous solution of sodium hexametaphosphate as a dispersion medium by means of a laser diffraction particle size distribution analyzer (SALD-2100 manufactured by Shimadzu Corporation). To be more specific about the electron microscope observation, for example, the average particle diameter can be determined by taking a photograph of particles by means of a scanning electron microscope (S-4000 manufactured by Hitachi, Ltd.) and measuring the particle diameters of (200 or more) particles observed in a unit area of field of view in the photograph by the use of an image-analyzing particle size distribution analysis software (Macview (Mountech Co., Ltd.)). In this case, the particle diameter of each particle is determined as an arithmetic mean of the maximum and minimum lengths of the particle, and, from the thus determined particle diameters and the number of the particles, the average primary particle diameter is calculated.

The filler (d) used in the present invention is less likely to aggregate and thus can be easily washed with water. Therefore, the use of the filler (d) of the present invention can reduce the contents of ionic impurities, such as an alkali metal, undergoing an acid-base reaction or chelation reaction with the acid group-containing (meth)acrylic polymerizable monomer (a).

The filler (d) can be obtained by surface-treating the filler (d) with the silane coupling agent (A) represented by the formula (1) and organosilazane (B) represented by the formula (2).

The surface treatment with the silane coupling agent (A) represented by the formula (1) substitutes the functional group derived from the silane coupling agent (A) for a hydroxy group existing on the surface of the filler (d).

The order of the surface treatment of the filler (d) is not particularly limited. For example, the silane coupling agent (A) represented by the formula (1) and organosilazane (B) represented by the formula (2) may be added sequentially or simultaneously to the filler (d) to surface-treat the filler (d) therewith. For example, the filler (d) may be reacted with the silane coupling agent (A) represented by the formula (1) first, subsequently with the organosilazane (B) represented by the formula (2). Alternatively, the filler (d) may be reacted with the organosilazane (B) represented by the formula (2) first, subsequently with the silane coupling agent (A) represented by the formula (1), and then with organosilazane (B) represented by the formula (2).

The method for surface-treating the filler (d) is not particularly limited as long as the method is a method for bonding the silane coupling agent (A) represented by the formula (1) to the surface of the filler (d) by a dehydration polycondensation reaction and a method for bonding the organosilazane (B) represented by the formula (2) to the surface of the filler (d) by a deammoniation reaction. Examples of the method for surface-treating the filler (d) include: a method in which the filler (d) is sprayed under stirring in a mixing chamber with solutions of the surface treatment agents each diluted with a solvent and dried by heating under continuous stirring in the chamber for a certain period of time; and a method in which the filler (d) and surface treatment agents are stirred and mixed in a solvent, followed by heat drying. Examples of the solvent include, but are not particularly limited to, alcohol solvents such as methanol, ethanol, and isopropanol, water, and a mixed solvent thereof. The heating temperature is not particularly limited, and may be around 30 to 90° C.

In the formula (1), $R^1$ is a hydrogen atom or methyl group. $R^2$ is an optionally substituted hydrolyzable group. $R^3$ is an optionally substituted $C_1$ to $C_3$ alkyl group. p is an integer of 1 to 13, preferably 2 to 10, more preferably 2 to 8, and even more preferably 2 to 6. q is 2 or 3, and preferably 3.

The optionally substituted hydrolyzable group represented by $R^2$ is not particularly limited. Examples of the hydrolyzable group include: linear or branched $C_1$ to $C_1$ alkoxy groups such as methoxy, ethoxy, n-propoxy, isopropoxy, n-butoxy, sec-butoxy, isobutoxy, tert-butoxy, pentyloxy, isopentyloxy, hexyloxy, and isohexyloxy groups; a chlorine atom; and isocyanate group. In view of hydrolyzability, the alkoxy group serving as the hydrolyzable group is more preferably a linear $C_1$ to $C_4$ alkoxy group selected from methoxy, ethoxy, n-propoxy, and n-butoxy groups, and even more preferably a linear $C_1$ to $C_3$ alkoxy group. The hydrolyzable group represented by $R^2$ may be unsubstituted.

It is preferable as the silane coupling agent (A) that in the formula (1), $R^1$ be a methyl group, $R^2$ be an unsubstituted $C_1$ to $C_6$ linear or branched alkoxy group, $R^3$ be an unsubstituted $C_1$ to $C_3$ alkyl group, p be 2 to 10, and q be 2 or 3. It is more preferable that in the formula (1), $R^1$ be a methyl group, $R^2$ be an unsubstituted linear or branched $C_1$ to $C_4$ alkoxy group, p be 2 to 8, and q be 3. It is even more preferable that in the formula (1), $R^1$ be a methyl group, $R^2$ be an unsubstituted linear or branched $C_1$ to $C_3$ alkoxy group, p be 2 to 6, and q be 3.

Examples of the optionally substituted $C_1$ to $C_3$ alkyl group represented by $R^3$, $R^4$, $R^5$, $R^6$, $R^7$, $R^8$, and $R^9$ include methyl, ethyl, n-propyl, and isopropyl groups. The alkyl group represented by $R^3$, $R^4$, $R^5$, $R^6$, $R^7$, $R^8$, and $R^9$ may be each individually unsubstituted. As the alkyl group represented by $R^4$, $R^5$, $R^6$, $R^7$, $R^8$, and $R^9$, methyl and ethyl groups are preferred, and a methyl group is more preferred. At least one of $R^4$, $R^5$, and $R^6$ is an optionally substituted $C_1$ to $C_3$ alkyl group, two of them may be an optionally substituted $C_1$ to $C_3$ alkyl group, all three of them may be an optionally substituted $C_1$ to $C_3$ alkyl group. At least one of $R^7$, $R^8$, and $R^9$ is an optionally substituted $C_1$ to $C_3$ alkyl group, two of them may be an optionally substituted $C_1$ to $C_3$ alkyl group, all three of them may be an optionally substituted $C_1$ to $C_3$ alkyl group.

Examples of a substituent in the hydrolyzable group represented by $R^2$ and a substituent in the alkyl group represented by $R^3$, $R^4$, $R^5$, $R^6$, $R^7$, $R^8$, and $R^9$ include a halogen atom (fluorine, chlorine, bromine, or iodine atom), carboxy group, hydroxy group, amino group, amino group mono- or di-substituted by a $C_1$ to $C_6$ alkyl group, acyl group, and $C_1$ to $C_6$ alkyl group. The number of the substituents is not particularly limited. The number of the substituents in the hydrolyzable group represented by $R^2$ is 1 to 5. The number of the substituents in the alkyl group represented by $R^3$, $R^4$, $R^5$, $R^6$, $R^7$, $R^8$ and $R^9$ is 1, 2, or 3.

Specific examples of the silane coupling agent (A) represented by the formula (1) include: (meth)acryloyloxymethyltrimethoxysilane, 2-(meth)acryloyloxyethyltrimethoxysilane, 3-(meth)acryloyloxypropyltrimethoxysilane, 4-(meth)acryloyloxybutyltrimethoxysilane, 5-(meth)acryloyloxypentyltrimethoxysilane, 6-(meth)acryloyloxyhexyltrimethoxysilane, 7-(meth)acryloyloxyheptyltrimethoxysilane, 8-(meth)acryloyloxyoctyltrimethoxysilane, 9-(meth)acryloyloxynonyltrimethoxysilane, 10-(meth)acryloyloxydecyltrimethoxysilane, 11-(meth)acryloyloxyundecyltrimethoxysilane, 11-(meth)acryloyloxyundecyldichloromethylsilane, 11-(meth)acryloyloxyundecyltrichlorosilane, 11-(meth)acryloyloxyundecyldimethoxymethylsilane, 12-(meth)acryloyloxydodecyltrimethoxysilane, and 13-(meth)acryloyloxytridecyltrimethoxysilane. One of these may be used alone, or two or more thereof can be used in appropriate combination. Among these, 2-methacryloyloxyethyltrimethoxysilane, 3-methacryloyloxypropyltrimethoxysilane, 4-methacryloyloxybutyltrimethoxysilane, 5-methacryloyloxypentyltrimethoxysilane, and 6-methacryloyloxyhexyltrimethoxysilane are preferred, and 3-methacryloyloxypropyltrimethoxysilane is more preferred, in that an adequately long alkylene group represented by $—(CH_2)_p—$ results in good compatibility with the polymerizable monomers in the multi-part dental cement and allows the content of the filler (d) comprised in the multi-part dental cement to be sufficiently increased, and that an adequately short alkylene group represented by $—(CH_2)_p—$ does not overly enhance the hydrophobicity and the bond strength is increased.

The organosilazane (B) is required to be bonded by a deammoniation reaction to the hydroxy group existing on the surface of the filler (d) and hydroxy group derived from the silane coupling agent (A). It is preferable to use the organosilazane (B) having a small molecular weight. Specific examples of the organosilazane (B) include: hexaethyldisilazane, hexa-n-propyldisilazane, hexaisopropyldisilazane, 1,1,2,2-tetramethyl-3,3-diethyldisilazane, 1,1,3,3-tetramethyldisilazane, 1,1,1,3,3,3-hexamethyldisilazane, and 1,1,1,3,3-pentamethyldisilazane. Preferred examples thereof include 1,1,3,3-tetramethyldisilazane, 1,1,1,3,3,3-hexamethyldisilazane, and 1,1,1,3,3-pentamethyldisilazane.

In the filler (d), the amount of the silane coupling agent (A) used for the treatment is preferably 0.5 to 15 parts by mass, more preferably 1 to 10 parts by mass, and particularly preferably 2 to 8 parts by mass, with respect to 100 parts by mass of the filler (d) yet to be surface-treated. If the amount of the silane coupling agent (A) used for the treatment is less than 0.5 parts by mass, the polymerizable group cannot be sufficiently imparted to the surface of the filler (d) and thus the mechanical strength may decrease.

In the surface treatment of the filler (d), the molar ratio between the silane coupling agent (A) and the organosilazane (B) is preferably [silane coupling agent (A)]:[organosilazane (B)]=1:1 to 1:20, and more preferably 1:2 to 1:10. If the molar amount of the organosilazane (B) is smaller than that of the silane coupling agent (A), aggregation may progress in the paste and the stability of the paste properties may not be ensured during a storage term. If the molar amount of the organosilazane (B) is more than 20 mol with respect to 1 mol of the silane coupling agent (A), the hydrophobicity may be increased and sufficient bond strength may be unachievable.

In the surface treatment step, a polymerization inhibitor may be added to reduce polymerization of the silane coupling agent (A). The polymerization inhibitor used can be a known polymerization inhibitor such as 3,5-dibutyl-4-hydroxytoluene (BHT) or p-methoxyphenol (methoquinone).

It is preferable that the surface treatment agent used in the surface treatment of the filler (d) consist essentially of the silane coupling agent (A) represented by the formula (1) and organosilazane (B) represented by the formula (2). If the surface treatment agent consists essentially of the silane coupling agent (A) and organosilazane (B), the content of a surface treatment agent component other than the silane coupling agent (A) and organosilazane (B) is less than 1.0 mass %, preferably less than 0.5 mass %, and more preferably less than 0.1 mass %.

Furthermore, the filler (d) is preferably solidified after undergoing the surface treatment. The solidification of the filler (d) is a step in which the filler (d) having undergone the surface treatment is precipitated using a mineral acid and the precipitate is washed with water and/or dehydrated (e.g., dried) to obtain solids of the filler (d). As previously described, a common filler surface-treated with a silane coupling agent (A) alone aggregates very easily, and it is thus very difficult to redisperse such a filler once the filler is solidified. However, since the filler (d) of the present invention is unlikely to aggregate, the filler (d) in a solid state is unlikely to aggregate. Even if the filler (d) of the present invention aggregates, redispersion is easy. As previously described, the filler (d) containing a small amount of ionic impurities such as an alkali metal can be easily produced by washing the filler (d) with water. The use of the filler (d) containing a small amount of ionic impurities makes it possible to further reduce possible occurrence of an interaction between the ionic impurities and, for example, a proton (H+) yielded from the acid group-containing (meth) acrylic polymerizable monomer (a), a hydroxy group (—OH) contained in another polymerizable monomer, or a very small amount of the remaining silanol group on the filler surface, and to further reduce changes in paste properties. In the washing step, the washing is preferably repeated until the electric conductivity of extract water (for example, water in which the filler (d) was immersed at 121° C. for 24 hours) of the filler (d) reaches 50 µS/cm or less.

Examples of the mineral acid used in the solidification include inorganic acids such as hydrochloric acid, nitric acid, sulfuric acid, and phosphoric acid, and hydrochloric acid is particularly preferred. The mineral acid may be used as it is, and is preferably used in the form of an aqueous mineral acid solution. The concentration of the mineral acid in the aqueous mineral acid solution is preferably 0.1 mass % or more and more preferably 0.5 mass % or more. The amount of the aqueous mineral acid solution can be about 6 to 12 times larger with respect to the mass of the filler (d) to be washed.

The washing with the aqueous mineral acid solution can be performed a plurality of times. In the washing with the aqueous mineral acid solution, the filler (d) is preferably immersed in the aqueous mineral acid solution, followed by stirring. The filler (d) immersed may be left for 1 to 24 hours or even about 72 hours. The stirring may be continued or may not be continued while the filler (d) is left. The washing in a mineral acid-containing liquid can also be performed under heating to ordinary temperature or higher. Thereafter, the filler (d) is collected by filtration and then washed with water. Water used in the washing preferably contains no ions (for example, 1 ppm or less on a mass basis) of, for example, an alkali metal. Preferred examples include ion-exchange water, distilled water, and pure water. In the washing with water, as is the case for the washing with the aqueous mineral acid solution, the filler (d) may be dispersed and suspended, followed by collection by filtration. Alternatively, water may continuously go through the filler (d) collected. The end of the washing with water may be determined from the above-described electric conductivity of extract water. Alternatively, the end of the washing with water may be when the concentration of an alkali metal in discharged water resulting from the washing of the filler (d) reaches 1 ppm or less, or may be when the concentration of an alkali metal in extract water reaches 5 ppm or less. The washing with water can also be performed under heating to ordinary temperature or higher.

The filler (d) can be dried in a conventional manner. For example, the filler (d) is heated, or left under reduced pressure (vacuum). A heating apparatus and pressure reducing apparatus are not particularly limited, and known apparatuses can be used.

Except for drying, the following method can be used as a method for dehydrating the filler (d): After an aqueous organic solvent having a boiling point higher than that of water is added to the filler (d) containing water, a mixture material soluble in the aqueous organic solvent is mixed in the aqueous organic solvent, and water is removed. Examples of the aqueous organic solvent include propylene glycol monomethyl ether (propylene glycol-1-methyl ether having a boiling point around 119° C.; propylene glycol-2-methyl ether having a boiling point around 130° C.), butanol (having a boiling point of 117.7° C.), N-methyl-2-pyrrolidone (having a boiling point around 204° C.), γ-butyrolactone (having a boiling point around 204° C.).

The content of the filler (d) is preferably in the range of 1 to 200 parts by mass, more preferably in the range of 1 to 190 parts by mass, and particularly preferably in the range of 1 to 150 parts by mass, with respect to 100 parts by mass of the total polymerizable monomers in the first paste. When the content of the filler (d) is in these ranges, the stability of the paste properties can be achieved during long-term storage.

The first paste of the multi-part dental cement of the present invention further comprises the acid group-containing (meth)acrylic polymerizable monomer (a). In the present invention, the (meth)acrylic polymerizable monomer refers to a (meth)acrylate polymerizable monomer and/or (meth)acrylamide polymerizable monomer.

The acid group-containing (meth)acrylic polymerizable monomer (a) is an essential component for the dental cement of the present invention to exhibit adhesiveness. The acid group-containing (meth)acrylic polymerizable monomer (a) has the effect of demineralizing tooth structures. The acid group-containing (meth)acrylic polymerizable monomer (a) is a polymerizable monomer having at least one acid group such as a phosphoric group, phosphonic group, pyrophosphoric group, carboxylic group, or sulfonic acid group and having at least one polymerizable group such as an acryloyl group, methacryloyl group, acrylamide group, or methacrylamide group. In view of adhesion to tooth structures, the acid group-containing (meth)acrylic polymerizable monomer (a) is preferably a monofunctional monomer having any one of acryloyl, methacryloyl, acrylamide, and methacrylamide groups as a polymerizable group. Specific examples thereof are as follows.

Examples of the phosphoric acid group-containing (meth)acrylic polymerizable monomer include: phosphoric acid group-containing monofunctional (meth)acrylate compounds such as 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyeicosyl dihydrogen phosphate, 2-(meth)acryloyloxyethylphenyl hydrogen phosphate, 2-(meth)acryloyloxyethyl-2-bromoethyl hydrogen phosphate, 2-(meth)acryloyloxyethyl-(4-methoxyphenyl) hydrogen phosphate, and 2-(meth)acryloyloxypropyl-(4-methoxyphenyl) hydrogen phosphate; their acid chlorides, alkali metal salts, ammonium salts, and amine salts; phosphoric acid group-containing difunctional (meth)acrylate compounds such as bis[2-(meth)acryloyloxyethyl] hydrogen phosphate, bis[4-(meth)acryloyloxybutyl] hydrogen phosphate, bis[6-(meth)acryloyloxyhexyl] hydrogen phosphate, bis[8-(meth)acryloyloxyoctyl] hydrogen phosphate, bis[9-(meth)acryloyloxynonyl] hydrogen phosphate, bis[10-(meth)acryloyloxydecyl] hydrogen phosphate, and 1,3-di(meth)acryloyloxypropyl dihydrogen phosphate; and their acid chlorides, alkali metal salts, ammonium salts, and amine salts.

Examples of the phosphonic acid group-containing (meth)acrylic polymerizable monomer include 2-(meth)acryloyloxyethylphenyl phosphonate, 5-(meth)acryloyloxypentyl-3-phosphonopropionate, 6-(meth)acryloyloxyhexyl-3-phosphonopropionate, 10-(meth)acryloyloxydecyl-3-phosphonopropionate, 6-(meth)acryloyloxyhexylphosphonoacetate, 10-(meth)acryloyloxydecylphosphonoacetate, and their acid chlorides, alkali metal salts, ammonium salts, and amine salts.

Examples of the pyrophosphoric acid group-containing (meth)acrylic polymerizable monomer include bis[2-(meth)acryloyloxyethyl] pyrophosphate, bis[4-(meth)acryloyloxybutyl] pyrophosphate, bis[6-(meth)acryloyloxyhexyl] pyrophosphate, bis[8-(meth)acryloyloxyoctyl] pyrophosphate, bis[10-(meth)acryloyloxydecyl] pyrophosphate, and their acid chlorides, alkali metal salts, ammonium salts, and amine salts.

Examples of the carboxylic acid group-containing (meth)acrylic polymerizable monomer include (meth)acrylic acid, 4-[2-[(meth)acryloyloxy]ethoxycarbonyl]phthalic acid, 4-(meth)acryloyloxyethyltrimellitic acid, 4-(meth)acryloyloxybutyloxycarbonylphthalic acid, 4-(meth)acryloyloxyhexyloxycarbonylphthalic acid, 4-(meth)acryloyloxyoctyloxycarbonylphthalic acid, 4-(meth)acryloyloxydecyloxycarbonylphthalic acid, their acid anhydrides, 5-(meth)acryloylaminopentylcarboxylic acid, 6-(meth)acryloyloxy-1,1-hexanedicarboxylic acid, 8-(meth)acryloyloxy-1,1-octane dicarboxylic acid, 10-(meth)acryloyloxy-1,1-decanedicarboxylic acid, 11-(meth)acryloyloxy-1,1-undecanedicarboxylic acid, and their acid chlorides, alkali metal salts, ammonium salts, and amine salts.

Examples of the sulfonic acid group-containing (meth)acrylic polymerizable monomer include 2-(meth)acrylamide-2-methylpropanesulfonic acid, 2-sulfoethyl (meth)acrylate, and their acid chlorides, alkali metal salts, ammonium salts and amine salts.

Among the examples of the acid group-containing (meth)acrylic polymerizable monomer (a), the phosphoric acid group-containing (meth)acrylic polymerizable monomer, pyrophosphoric acid group-containing (meth)acrylic polymerizable monomer, and carboxylic acid group-containing (meth)acrylic polymerizable monomer are preferred since such monomers provide better bond strength to tooth structures. The phosphoric acid group-containing (meth)acrylic polymerizable monomer and carboxylic acid group-containing (meth)acrylic polymerizable monomer are particularly preferred. Among these, a phosphoric acid group-containing monofunctional (meth)acrylate polymerizable monomer having as the main chain of the molecule a $C_6$ to $C_{20}$ alkyl group or $C_6$ to $C_{20}$ alkylene group and carboxylic acid group-containing (meth)acrylate polymerizable monomer having as the main chain of the molecule a $C_6$ to $C_{20}$ alkyl group or $C_6$ to $C_{20}$ alkylene group are more preferred, and a phosphoric acid group-containing monofunctional (meth)acrylate polymerizable monomer having as the main chain of the molecule a $C_8$ to $C_{20}$, alkylene group is even more preferred. Preferred are 10-methacryloyloxydecyl dihydrogen phosphate, 4-(meth)acryloyloxyethyltrimellitic acid, and 4-(meth)acryloyloxyethyltrimellitic acid anhydride, and most preferred are 10-methacryloyloxydecyl dihydrogen phosphate.

As the acid group-containing (meth)acrylic polymerizable monomer (a), one of the above monomers may be contained alone, or two or more thereof may be contained in combination. The content of the acid group-containing (meth)acrylic polymerizable monomer (a) is not particularly limited as long as the effect of the present invention can be obtained. In order to obtain higher bond strength, the content of the acid group-containing (meth)acrylic polymerizable monomer (a) is preferably in the range of 1 to 50 parts by mass, more preferably in the range of 1 to 30 parts by mass, and most preferably in the range of 2 to 10 parts by mass, in 100 parts by mass of the total polymerizable monomer components in the first paste. In the present specification, the content of a polymerizable monomer in 100 parts by mass of the total polymerizable monomer components refers to the content (mass %) of the polymerizable monomer in 100 mass % of the sum of the amounts of the polymerizable monomer components. Thus, the sum of the amounts of the polymerizable monomer components does not exceed 100 parts by mass.

The first paste and second paste of the multi-part dental cement of the present invention comprise the polyfunctional (meth)acrylic polymerizable monomer (b) containing no acid group. The polyfunctional (meth)acrylic polymerizable monomer (b) containing no acid group has no acid group and has at least two polymerizable groups per molecule. The polyfunctional (meth)acrylic polymerizable monomer (b) containing no acid group has the effect of improving the handling properties or mechanical strength of the dental cement of the present invention. Examples of the polyfunctional (meth)acrylic polymerizable monomer (b) containing no acid group include difunctional aromatic polymerizable monomers, difunctional aliphatic polymerizable monomers, and tri- or higher-functional polymerizable monomers.

Examples of the difunctional aromatic polymerizable monomer include difunctional (meth)acrylate compounds such as 2,2-bis((meth)acryloyloxyphenyl)propane, 2,2-bis[4-(3-(meth)acryloyloxy-2-hydroxypropoxy)phenyl]propane, 2,2-bis(4-(meth)acryloyloxyethoxyphenyl)propane, 2,2-bis(4-(meth)acryloyloxypolyethoxyphenyl)propane (having an average number of moles of added ethoxy groups of 2.6), 2,2-bis(4-(meth)acryloyloxydiethoxyphenyl)propane, 2,2-bis(4-(meth)acryloyloxytriethoxyphenyl)propane, 2,2-bis(4-(meth)acryloyloxytetraethoxyphenyl)propane, 2,2-bis(4-(meth)acryloyloxypentaethoxyphenyl)propane, 2,2-bis(4-(meth)acryloyloxydipropoxyphenyl)propane, 2-(4-(meth)acryloyloxydiethoxyphenyl)-2-(4-(meth)acryloyloxyethoxyphenyl)propane, 2-(4-(meth)acryloyloxydiethoxyphenyl)-2-(4-(meth)acryloyloxytriethoxyphenyl)propane, 2-(4-(meth)acryloyloxydiprop oxyphenyl)-2-(4-(meth)acryloyloxytriethoxyphenyl)propane, 2,2-bis(4-(meth)acryloyloxypropoxyphenyl)propane, and 2,2-bis(4-(meth)acryloyloxyisopropoxyphenyl)propane.

Examples of the difunctional aliphatic polymerizable monomer include difunctional (meth)acrylate compounds such as glycerol di(meth)acrylate, ethylene glycol di(meth)acrylate, diethylene glycol di(meth)acrylate, triethylene glycol di(meth)acrylate, propylene glycol di(meth)acrylate, butylene glycol di(meth)acrylate, neopentyl glycol di(meth) acrylate, 1,3-butanediol di(meth)acrylate, 1,5-pentanediol di(meth)acrylate, 1,6-hexanediol di(meth)acrylate, 1,10-decanediol di(meth)acrylate, 2,2,4-trimethylhexamethylene bis(2-carbamoyloxyethyl) di(meth)acrylate, and 1,2-bis(3-methacryloyloxy-2-hydroxypropoxy)ethane.

Examples of the tri- or higher-functional polymerizable monomer include tri- or higher-functional (meth)acrylate compounds such as trimethylolpropane tri(meth)acrylate, trimethylolethane tri(meth)acrylate, trimethylolmethane tri(meth)acrylate, pentaerythritol tri(meth)acrylate, pentaerythritol tetra(meth)acrylate, dipentaerythritol penta(meth)acrylate, N,N'-(2,2,4-trimethylhexamethylene)bis[2-(aminocarboxy)propane-1,3-diol] tetra(meth)acrylate, and 1,7-diacryloyloxy-2,2,6,6-tetra(meth)acryloyloxymethyl-4-oxaheptane. Among these, N,N'-(2,2,4-trimethylhexamethylene)bis[2-(aminocarboxy)propane-1,3-diol] tetramethacrylate is preferred.

Among the examples of the polyfunctional (meth)acrylic polymerizable monomer (b) containing no acid group, the difunctional aromatic polymerizable monomer and difunctional aliphatic polymerizable monomer are preferably used in view of the mechanical strength or handling properties. Preferred examples of the difunctional aromatic polymerizable monomer are 2,2-bis[4-(3-(methacryloyloxy-2-hydroxypropoxy)phenyl]propane (commonly known as "BisGMA") and 2,2-bis(4-methacryloyloxypolyethoxyphenyl) propane (preferably having an average number of moles of added ethoxy groups of 2.6, commonly known as "D-2.6E"). Preferred examples of the difunctional aliphatic polymerizable monomer are glycerol di(meth)acrylate, triethylene glycol diacrylate, triethylene glycol dimethacrylate (commonly known as "TEGDMA"), neopentyl glycol di(meth) acrylate, 1,6-hexanediol di(meth)acrylate, 1,10-decanediol di(meth)acrylate, 1,2-bis[3-methacryloyloxy-2-hydroxypropoxy]ethane, and 2,2,4-trimethylhexamethylenebis(2-carbamoyloxyethyl) dimethacrylate (commonly known as "UDMA").

Among the examples of the polyfunctional (meth)acrylic polymerizable monomer (b) containing no acid group, BisGMA, D-2.6E, and TEGDMA are more preferred.

As the polyfunctional (meth)acrylic polymerizable monomer (b) containing no acid group, one of the above monomers may be contained alone, or two or more thereof may be contained in combination. The content of the polyfunctional (meth)acrylic polymerizable monomer (b) containing no acid group is not particularly limited as long as the effect of the present invention can be obtained. In order to provide the composition with high penetrability into a tooth structure, excellent bond strength, and sufficient strength, the content of the polyfunctional (meth)acrylic polymerizable monomer (b) containing no acid group is preferably in the range of 30 to 95 parts by mass, more preferably in the range of 40 to 85 parts by mass, even more preferably in the range of 50 to 80 parts by mass, and most preferably in the range of 55 to 80 parts by mass, in 100 parts by mass of the total polymerizable monomer components in the dental cement (combination of the first paste and second paste).

Subsequently, the chemical polymerization initiator (c) will be described. The chemical polymerization initiator (c) can be selected for use from polymerization initiators used in general industrial fields and, in particular, chemical polymerization initiators for dental cements are preferably used.

The chemical polymerization initiator (c) used in the present invention consists of the oxidizing agent (c-1) (hereinafter, the oxidizing agent of the chemical polymerization initiator may be referred to as "chemical polymerization initiator (c-1)", and a compound with "(c-1)" attached refers to the oxidizing agent of the chemical polymerization initiator) and reducing agent (c-2) (hereinafter, the reducing agent of the chemical polymerization initiator may be referred to as "chemical polymerization initiator (c-2)", and a compound with "(c-2)" attached refers to the reducing agent of the chemical polymerization initiator). The first paste of the multi-part dental cement of the present invention comprises the oxidizing agent (c-1) of the chemical polymerization initiator, and the second paste comprises the reducing agent (c-2) of the chemical polymerization initiator.

Examples of the chemical polymerization initiator (c-1) include organic peroxides, azo compounds, and inorganic peroxides. Examples of the organic peroxide include diacyl peroxides, peroxyesters, dialkyl peroxides, peroxyketals, ketone peroxides, and hydroperoxides. Specific examples of the diacyl peroxide include benzoyl peroxide, 2,4-dichlorobenzoyl peroxide, and m-toluoyl peroxide. Specific examples of the peroxyester include t-butyl peroxybenzoate, bis(t-butyl peroxy)isophthalate, 2,5-dimethyl-2,5-bis(benzoylperoxy)hexane, t-butyl peroxy-2-ethylhexanoate, and t-butylperoxyisopropyl carbonate. Specific examples of the dialkyl peroxide include dicumyl peroxide, di-t-butyl peroxide, and lauroyl peroxide. Specific examples of the peroxyketal include 1,1-bis(t-butylperoxy) 3,3,5-trimethylcyclohexane, 1,1-bis(t-butylperoxy)cyclohexane, and 1,1-bis (t-hexylperoxy)cyclohexane. Specific examples of the ketone peroxide include methyl ethyl ketone peroxide, cyclohexanone peroxide, and methyl acetoacetate peroxide. Specific examples of the hydroperoxide include t-butyl hydroperoxide, cumene hydroperoxide, p-diisopropylbenzene hydroperoxide, and 1,1,3,3-tetramethylbutyl hydroperoxide. Examples of the azo compound include 2,2'-azobis (isobutyronitrile), 2,2'-azobis(4-methoxy-2,4-dimethylvaleronitrile, and 2,2'-azobis(2,4-dimethylvaleronitrile). Examples of the inorganic peroxide include sodium persulfate, potassium persulfate, aluminum persulfate, and ammonium persulfate. As the oxidizing agent (c-1), one of these may be used alone, or two or more thereof may be used in combination.

Examples of the chemical polymerization initiator (c-2) include aromatic amines without an electron withdrawing group in the aromatic ring, thiourea compounds, and ascorbic acids. Examples of the aromatic amine without an electron withdrawing group in the aromatic ring include N,N-bis(2-hydroxyethyl)-3,5-dimethylaniline, N,N-bis(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-di-t-butylaniline, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, and N,N-dimethyl-3,5-di-t-butylaniline. One of the above aromatic amines without an electron withdrawing group in the aromatic ring may be used alone, or two or more thereof may be used in combination. Examples of the thiourea compound include thiourea, methylthiourea, ethylthiourea, ethylenethiourea, N,N'-dimethylthiourea, N,N'-diethylthiourea, N,N'-di-n-propylthiourea, N,N'-dicyclohexylthiourea, trimethylthiourea, triethylthiourea, tri-n-propylthiourea, tricyclohexylthiourea, tetramethylthiourea, tetraethylthiourea, tetra-n-propylthiourea, tetracyclohexylthiourea, 1-(2-pyridyl)-2-thiourea, and 4,4-dimethylethylenethiourea. One of the thiourea compounds may be used alone, or two or more thereof may be used in combination.

Among these examples of the chemical polymerization initiators (c-1) and (c-2), a combination of the hydroperoxide as the oxidizing agent (c-1) and the thiourea compound as the reducing agent (c-2) and a combination of the diacyl peroxide and/or inorganic peroxide as the oxidizing agent (c-1) and the aromatic amine without an electron withdrawing group in the aromatic ring as the reducing agent (c-2) are preferably used in view of the curability of the resultant composition.

The total content of the chemical polymerization initiators (c-1) and (c-2) as the chemical polymerization initiator (c) is not particularly limited. In view of the mechanical strength and bond strength of the resultant dental cement, the total content of the chemical polymerization initiators (c-1) and (c-2) is preferably 0.01 to 20 parts by mass, more preferably 0.05 to 10 parts by mass, and most preferably 0.1 to 5 parts by mass, with respect to 100 parts by mass of the total polymerizable monomers.

In an embodiment, the second paste of the dental cement of the present invention may comprise the filler (e) identical to the filler (d). That is, in this embodiment, the filler (e) comprised in the second paste may be surface-treated with the silane coupling agent (A) and organosilazane (B). In another embodiment, the filler (e) comprised in the second paste may be surface-treated with the organosilazane (B) alone. In this embodiment, the filler (e) may also be comprised in the first paste as long as a change in the paste properties and the solidification risk are not affected during long-term storage. In another preferred embodiment, the second paste of the dental cement of the present invention comprises the filler (e) which is not the filler (d). In this preferred embodiment, the filler (e) may be at least not surface-treated with the organosilazane (B). In this preferred embodiment, the filler (e) may be surface-treated with the silane coupling agent (A) because in that case, the dental cement has better mechanical strength. In this preferred embodiment, the filler (e) at least not surface-treated with the organosilazane (B) may also be comprised in the first paste as long as a change in the paste properties and the solidification risk are not affected during long-term storage. The filler (e) is a component for imparting the X-ray opacity to the dental cement or for improving the dental cement in strength as a matrix or handling properties as a paste.

The term "X-ray opacity" as used in the present specification refers to the ability of a cured dental material distinguished from the structure of a tooth using a dental X-ray apparatus commonly used in conventional methods. The radiopacity of dental materials is advantageous in a particular case where the tooth condition is diagnosed by X-ray.

As the filler (e), any known filler used in radical polymerization curable compositions for dental use, except for those prepared by flame pyrolysis, can be used without any limitation. Examples of the filler include: various types of glasses [containing silica as a main component and optionally containing oxides of heavy metals, boron, aluminum, etc., for example: glass powders having typical compositions, such as fused silica, quartz, soda lime silica glass, E-glass, C-glass, borosilicate glass (Pyrex (registered trademark) glass); and glass powders for dental use, such as barium glass (GM 27884 and 8235 manufactured by Schott, and E-2000 and E-3000 manufactured by Esstech, Inc.), strontium borosilicate glass (E-4000 manufactured by Esstech, Inc.), lanthanum glass ceramics (GM 31684 manufactured by Schott), and fluoroaluminosilicate glass (GM 35429, G018-091, and G018-117 manufactured by Schott)]; various types of ceramics; composite oxides such as silica-titania and silica-zirconia; diatomaceous earth; kaolin; clay minerals (such as montmorillonite); activated white clay; synthetic zeolite; mica; calcium fluoride; ytterbium fluoride; yttrium fluoride; calcium fluoride having the surface coated with silica and having a core-shell structure; ytterbium fluoride having the surface coated with silica and having a core-shell structure; yttrium fluoride having the surface coated with silica and having a core-shell structure; calcium phosphate; barium sulfate; zirconium dioxide; titanium dioxide; hydroxyapatite; calcium phosphate having the surface coated with silica and having a core-shell structure; barium sulfate having the surface coated with silica and having a core-shell structure; zirconium dioxide having the surface coated with silica and having a core-shell structure; titanium dioxide having the surface coated with silica and having a core-shell structure; and hydroxyapatite having the surface coated with silica and having a core-shell structure. One of these may be used alone, or two or more thereof can be used in mixture. Among these, ytterbium fluoride having the surface coated with silica and having a core-shell structure and yttrium fluoride having the surface coated with silica and having a core-shell structure are suitable because they contribute to showing the X-ray opacity at a small amount and can be treated with the silane coupling agent (A). It is not preferable to add a filler prepared by flame pyrolysis because, in that case, thixotropy attributable to a hydroxy group or the like on the surface of such a filler having a large specific surface area is exhibited remarkably and thus a problem occurs in that the paste properties exhibited just after preparation of the paste and those exhibited after storage of the paste are greatly different. Commercially-available fillers prepared by flame pyrolysis are, for example, AEROSIL, AEROXIDE Alu C, AEROXIDE $TiO_2$ P 25, AEROXIDE $TiO_2$ P 25, VP Zirconium Oxide 3-YSZ, and VP Zirconium Oxide 3-YSZ PH, which are trade names and manufactured by Nippon Aerosil Co., Ltd.

The average particle diameter of the filler (e) is preferably 0.01 to 50.0 μm, more preferably 0.05 to 20.0 μm, even more preferably 0.08 to 10.0 μm, and particularly preferably 0.10 to 4.50 μm. When the average particle diameter of the filler (e) is within these ranges, sufficient mechanical strength can be obtained, and the paste does not become sticky and thus has good handling properties. In addition, the resultant cured product has high surface smoothness and gloss after polishing and good retention of the smoothness and gloss. In the present specification, the average particle diameter of the filler means the average particle diameter (average primary particle diameter) of the primary particles of the filler.

The average particle diameter of the filler (e) can be measured in the same manner as the method for measuring the average particle diameter of the filler (d).

The filler (e) is preferably surface-treated with a surface treatment agent beforehand in order to improve the compatibility with the polymerizable monomer components and to increase the chemical bonding to the polymerizable monomer components so as to increase the mechanical strength of the resultant cured product.

Examples of the surface treatment agent include at least one organometallic compound selected from the group consisting of organosilicon compounds, organotitanium compounds, organozirconium compounds, and organoaluminum compounds. When two or more organometallic compounds are used, the resultant surface-treated layer may be composed of a mixture of the two or more organometallic compounds or may have a multilayer structure composed of two or more stacked layers respectively consisting of the organometallic compounds.

Examples of the organosilicon compound include compounds represented by $W_nSiY_{4-n}$, wherein W is a substituted or unsubstituted $C_1$ to $C_{12}$ hydrocarbon group, Y represents a $C_1$ to $C_4$ alkoxy group, a hydroxy group, a halogen atom, or a hydrogen atom, and n is an integer of 0, 1, 2, or 3. When there are two or more W and two or more Y, the two or more W may be the same as or different from each other, and the two or more Y may be the same as or different from each other.

Specific examples of the organosilicon compound include methyltrimethoxysilane, dimethyldimethoxysilane, phenyltrimethoxysilane, diphenyldimethoxysilane, methyltriethoxysilane, dimethyldiethoxysilane, phenyltriethoxysilane, diphenyldiethoxysilane, isobutyltrimethoxysilane, vinyltrimethoxysilane, vinyltriethoxysilane, vinyltris(ß-methoxyethoxy)silane, 3,3,3-trifluoropropyltrimethoxysilane, methyl-3,3,3-trifluoropropyldimethoxysilane, ß-(3,4-epoxycyclohexy)ethyltrimethoxysilane, γ-glycidoxypropyltrimethoxysilane, γ-glycidoxypropylmethyldiethoxysilane, γ-glycidoxypropyltriethoxysilane, γ-methacryloyloxypropylmethyldimethoxysilane, γ-methacryloyloxypropylmethyldiethoxysilane, N-ß-(aminoethyl)-γ-aminopropylmethyldimethoxysilane, N-ß-(aminoethyl)-γ-aminopropyltrimethoxysilane, N-ß-(aminoethyl)-γ-aminopropyltriethoxysilane, γ-aminopropyltrimethoxysilane, γ-aminopropyltriethoxysilane, N-phenyl-γ-aminopropyltrimethoxysilane, γ-mercaptopropyltrimethoxysilane, trimethylsilanol, methyltrichlorosilane, methyldichlorosilane, dimethylclichlorosilane, trimethylchlorosilane, phenyltrichlorosilane, diphenyldichlorosilane, vinyltrichlorosilane, trimethylbromosilane, diethylsilane, vinyltriacetoxysilane, ω-(meth)acryloyloxyalkyltrimethoxysilane (the number of carbon atoms between the (meth)acryloyloxy group and the silicon atom: 3 to 12, e.g., γ-methacryloyloxypropyltrimethoxysilane), and ω-(meth)acryloyloxyalkyltriethoxysilane (the number of carbon atoms between the (meth)acryloyloxy group and the silicon atom: 3 to 12, e.g., γ-methacryloyloxypropyltriethoxysilane).

Among these, a coupling agent having a functional group copolymerizable with the above polymerizable monomer components is particularly preferably used, and examples thereof include ω-(meth)acryloyloxyalkyltrimethoxysilane (the number of carbon atoms between the (meth)acryloyloxy group and the silicon atom: 3 to 12), ω-(meth)acryloyloxyalkyltriethoxysilane (the number of carbon atoms between the (meth)acryloyloxy group and the silicon atom: 3 to 12), vinyltrimethoxysilane, vinyltriethoxysilane, vinyltriacetoxysilane, and γ-glycidoxypropyltrimethoxysilane.

Examples of the organotitanium compound include tetramethyl titanate, tetraisopropyl titanate, tetra-n-butyl titanate, butyl titanate dimer, and tetra(2-ethylhexyl) titanate.

Examples of the organozirconium compound include zirconium isopropoxide, zirconium n-butoxide, zirconium acetylacetonate, and zirconyl acetate.

Examples of the organoaluminum compound include aluminum acetylacetonate and a chelate compound of a salt of aluminum and an organic acid.

The shape of the filler (e) is not particularly limited. The shape of the filler (e) may be selected as appropriate depending on a property intended to be improved of the dental cement. Specifically, the filler (e) can be used in the form of a powder consisting of irregular-shaped or spherical particles. When the irregular-shaped filler (e) is used, the mechanical strength and wear resistance are particularly improved. When the spherical filler (e) is used, the surface smoothness and gloss after polishing and the retention of the smoothness and gloss are particularly improved. A commercially available filler may be used as the filler (e) of the present invention.

The content of the filler (e) in the dental cement of the present invention is not particularly limited as long as the effect of the present invention can be obtained. The content of the filler (e) is preferably in the range of 1 to 200 parts by mass, more preferably in the range of 3 to 180 parts by mass, and particularly preferably in the range of 5 to 150 parts by mass, with respect to 100 parts by mass of the total polymerizable monomers. When the content of the filler (e) is in these ranges, both sufficient X-ray opacity or sufficient mechanical strength of the resultant cured product and sufficient paste handling properties can be obtained.

The dental cement of the present invention comprises the chemical polymerization initiator (c). As a component other than the chemical polymerization initiator (c), a conventionally known photopolymerization initiator (f) may be further added to at least one of the pastes of the multi-part dental cement of the present invention so as to form a dual cure type composition whose polymerization is initiated upon irradiation with light. Examples of the photopolymerization initiator (f) include photopolymerization initiators that may be used in dental cements. Such photopolymerization initiators are, for example, (bis)acylphosphine oxides, water-soluble acylphosphine oxides, thioxanthones, quaternary ammonium salts of thioxanthones, ketals, α-diketones, coumarins, anthraquinones, benzoin alkyl ether compounds, and α-aminoketone compounds. Among these, at least one selected from the group consisting of (bis)acylphosphine oxides and α-diketones is preferably used. Among (bis)acylphosphine oxides, 2,4,6-trimethylbenzoylcliphenylphosphine oxide is particularly preferably used, and among α-diketones, camphorquinone is particularly preferably used.

The content of the photopolymerization initiator W is not particularly limited. In view of, for example, the curability of the resultant dental cement, the content of the photopolymerization initiator (f) is preferably 0.001 to 10 parts by mass, more preferably 0.005 to 5 parts by mass, and most preferably 0.01 to 3 parts by mass, with respect to 100 parts by mass of the total polymerizable monomer components.

In a preferred embodiment of the present invention, the chemical polymerization initiator (c) and photopolymerization initiator (f) are used in combination with a polymerization accelerator (g). The polymerization accelerator (g) may be added to at least one paste of the multi-part dental cement of the present invention. Examples of the polymerization accelerator (g) used in the present invention include aliphatic amines, aromatic tertiary amines having an electron withdrawing group, sulfinic acids, salts of sulfinic acids, sulfur-containing reducing inorganic compounds, borate compounds, barbituric acid derivatives, triazine compounds, copper compounds, tin compounds, vanadium compounds, halogen compounds, aldehydes, and thiol compounds.

Examples of the aliphatic amine include: primary aliphatic amines such as n-butylamine, n-hexylamine, and n-octylamine; secondary aliphatic amines such as diisopropylamine, dibutylamine, and N-methylethanolamine; tertiary aliphatic amines such as N-methyldiethanolamine, N-ethyldiethanolamine, N-n-butyldiethanolamine, N-lauryldiethanolamine, 2-(dimethylamino)ethyl (meth)acrylate, N-methyldiethanolamine di(meth)acrylate, N-ethyldiethanolamine di(meth)acrylate, triethanolamine mono(meth)acrylate, triethanolamine di(meth)acrylate, triethanolamine tri(meth)acrylate, triethanolamine, trimethylamine, triethylamine, and tributylamine. Among these, tertiary aliphatic amines are preferred in view of the curability and storage stability of the resultant composition, and in particular, N-methyldiethanolamine and triethanolamine are preferred.

Examples of the aromatic tertiary amine having an electron withdrawing group include compounds in which a hydrogen atom of the aromatic ring of the aromatic tertiary amine is substituted by an electron withdrawing group such as a carboxyl group, carboxylic ester group, nitrile group, or halogen group. Specific examples of such a compound include ethyl 4-(N,N-dimethylamino)benzoate, methyl 4-(N,N-dimethylamino)benzoate, propyl 4-(N,N-dimethylamino)benzoate, n-butoxyethyl 4-(N,N-dimethylamino)benzoate, 2-[(meth)acryloyloxy]ethyl 4-(N,N-dimethylamino)benzoate, and 4-(N,N-dimethylamino)benzophenone. Among these, ethyl 4-(N,N-dimethylamino)benzoate, methyl 4-(N,N-dimethylamino)benzoate, n-butoxyethyl 4-(N,N-dimethylamino)benzoate, and 4-(N,N-dimethylamino)benzophenone are preferred in view of the curability of the resultant composition.

Examples of the sulfinic acids and salts of sulfinic acids include p-toluenesulfinic acid, sodium p-toluenesulfinate, potassium p-toluenesulfinate, lithium p-toluenesulfinate, calcium p-toluenesulfinate, benzenesulfinic acid, sodium benzenesulfinate, potassium benzenesulfinate, lithium benzenesulfinate, calcium benzenesulfinate, 2,4,6-trimethylbenzenesulfinic acid, sodium 2,4,6-trimethylbenzenesulfinate, potassium 2,4,6-trimethylbenzenesulfinate, lithium 2,4,6-trimethylbenzenesulfinate, calcium 2,4,6-trimethylbenzenesulfinate, 2,4,6-triethylbenzenesulfinic acid, sodium 2,4,6-triethylbenzenesulfinate, potassium 2,4,6-triethylbenzenesulfinate, lithium 2,4,6-triethylbenzenesulfinate, calcium 2,4,6-triethylbenzenesulfinate, 2,4,6-triisopropylbenzenesulfinic acid, sodium 2,4,6-triisopropylbenzenesulfinate, potassium 2,4,6-triisopropylbenzenesulfinate, lithium 2,4,6-triisopropylbenzenesulfinate, and calcium 2,4,6-triisopropylbenzenesulfinate.

Examples of the sulfur-containing reducing inorganic compound include sulfurous acid salts, bisulfurous acid salts, pyrosulfurous acid salts, thiosulfuric acid salts, thionic acid salts, and dithionous acid salts. Specific examples thereof include sodium sulfite, potassium sulfite, calcium sulfite, ammonium sulfite, sodium hydrogen sulfite, and potassium hydrogen sulfite.

The borate compound is preferably an aryl borate compound. Specific examples of the aryl borate compound suitably used include borate compounds having one aryl group per molecule, such as: trialkylphenylboron, trialkyl(p-chlorophenyl)boron, trialkyl(p-fluorophenyl)boron, trialkyl[3,5-bis(trifluoromethyl)phenyl]boron, trialkyl[3,5-bis(1,1,1,3,3,3-hexafluoro-2-methoxy-2-propyl)phenyl]boron, trialkyl(p-nitrophenyl)boron, trialkyl(m-nitrophenyl)boron, trialkyl(p-butylphenyl)boron, trialkyl(m-butylphenyl)boron, trialkyl(p-butyloxyphenyl)boron, trialkyl(m-butyloxyphenyl)boron, trialkyl(p-octyloxyphenyl)boron, and trialkyl(m-octyloxyphenyl)boron (their alkyl groups are each at least one selected from the group consisting of, for example, an n-butyl group, n-octyl group, and n-dodecyl group); and their salts (such as sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts).

Examples of the aryl borate compound include borate compounds having two aryl groups per molecule, such as: dialkyldiphenylboron, dialkyldi(p-chlorophenyl)boron, dialkyldi(p-fluorophenyl)boron, dialkyl[di(3,5-bis(trifluoromethyl)phenyl]boron, dialkyldi[3,5-bis(1,1,1,3,3,3-hexafluoro-2-methoxy-2-propyl)phenyl]boron, dialkyldi(p-nitrophenyl)boron, dialkyldi(m-nitrophenyl)boron, dialkyldi(p-butylphenyl)boron, dialkyldi(m-butylphenyl)boron, dialkyldi(p-butyloxyphenyl)boron, dialkyldi(m-butyloxyphenyl)boron, dialkyldi(p-octyloxyphenyl)boron and dialkyldi(m-octyloxyphenyl)boron (their alkyl groups are each at least one selected from the group consisting of, for example, an n-butyl group, n-octyl group, and n-dodecyl group); and their salts (such as sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts).

Examples of the aryl borate compound further include borate compounds having three aryl groups per molecule, such as: monoalkyltriphenylboron, monoalkyltri(p-chlorophenyl)boron, monoalkyltri(p-fluorophenyl)boron, monoalkyltri[3,5-bis(trifluoromethyl)phenyl]boron, monoalkyltri[3,5-bis(1,1,1,3,3,3-hexafluoro-2-methoxy-2-propyl)phenyl]boron, monoalkyltri(p-nitrophenyl)boron, monoalkyltri(m-nitrophenyl)boron, monoalkyltri(p-butylphenyl)boron, monoalkyltri(m-butylphenyl)boron, monoalkyltri(p-butyloxyphenyl)boron, monoalkyltri(m-butyloxyphenyl)boron, monoalkyltri(p-octyloxyphenyl)boron, and monoalkyltri(m-octyloxyphenyl)boron (the alkyl group of each of them is one selected from, for example, an n-butyl group, n-octyl group, and n-dodecyl group); and their salts (such as sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts).

Examples of the aryl borate compound further include borate compounds having four aryl groups per molecule, such as: tetraphenylboron, tetrakis(p-chlorophenyl)boron, tetrakis(p-fluorophenyl)boron, tetrakis[3,5-bis(trifluoromethyl)phenyl]boron, tetrakis[3,5-bis(1,1,1,3,3,3-hexafluoro-2-methoxy-2-propyl)phenyl]boron, tetrakis(p-nitrophenyl)boron, tetrakis(m-nitrophenyl)boron, tetrakis(p-butylphenyl)boron, tetrakis(m-butylphenyl)boron, tetrakis(p-butyloxyphenyl)boron, tetrakis(m-butyloxyphenyl)boron, tetrakis(p-octyloxyphenyl)boron, tetrakis(m-octyloxyphenyl)boron, (p-fluorophenyl)triphenylboron, [3,5-bis(trifluoromethyl)phenyl] triphenylboron, (p-nitrophenyl)triphenylboron, (m-butyloxyphenyl)triphenylboron, (p-butyloxyphenyl)triphenylboron, (m-octyloxyphenyntriphenylboron, and (p-octyloxyphenyl)triphenylboron; and their salts (such as sodium salts, lithium salts, potassium salts, magnesium salts, tetrabutylammonium salts, tetramethylammonium salts, tetraethylammonium salts, methylpyriclinium salts, ethylpyridinium salts, butylpyridinium salts, methylquinolinium salts, ethylquinolinium salts, and butylquinolinium salts).

Examples of the barbituric acid derivative include: barbituric acid, 1,3-dimethylbarbituric acid, 1,3-diphenylbarbituric acid, 1,5-dimethylbarbituric acid, 5-butylbarbituric acid, 5-ethylbarbituric acid, 5-isopropylbarbituric acid, 5-cyclohexylbarbituric acid, 1,3,5-trimethylbarbituric acid, 1,3-dimethyl-5-ethylbarbituric acid, 1,3-dimethyl-5-n-butylbarbituric acid, 1,3-dimethyl-5-isobutylbarbituric acid, 1,3-dimethyl-5-cyclopentylbarbituric acid, 1,3-dimethyl-5-cyclohexylbarbituric acid, 1,3-dimethyl-5-phenylbarbituric acid, 1-cyclohexyl-1-ethylbarbituric acid, 1-benzyl-5-phenylbarbituric acid, 5-methylbarbituric acid, 5-propylbarbituric acid, 1,5-diethylbarbituric acid, 1-ethyl-5-methylbarbituric acid, 1-ethyl-5-isobutylbarbituric acid, 1,3-diethyl-5-butylbarbituric acid, 1-cyclohexyl-5-methylbarbituric acid, 1-cyclohexyl-5-ethylbarbituric acid, 1-cyclohexyl-5-octylbarbituric acid, 1-cyclohexyl-5-hexylbarbituric acid, 5-butyl-1-cyclohexylbarbituric acid, 1-benzyl-5-phenylbarbituric acid, and thiobarbituric acids; and their salts (alkali metal salts and alkaline earth metal salts are preferred). Examples of the salts of the barbituric acids include sodium 5-butylbarbiturate, sodium 1,3,5-trimethylbarbiturate, and sodium 1-cyclohexyl-5-ethylbarbiturate.

Examples of the triazine compound include 2,4,6-tris(trichloromethyl)-s-triazine, 2,4,6-tris(tribromomethyl)-s-triazine, 2-methyl-4,6-bis(trichloromethyl)-s-triazine, 2-methyl-4,6-bis(tribromomethyl)-s-triazine, 2-phenyl-4,6-bis(trichloromethyl)-s-triazine, 2-(p-methoxyphenyl)-4,6-bis(trichloromethyl)-s-triazine, 2-(p-methylthiophenyl)-4,6-bis(trichloromethyl)-s-triazine, 2-(p-chlorophenyl)-4,6-bis(trichloromethyl)-s-triazine, 2-(2,4-dichlorophenyl)-4,6-bis(trichloromethyl)-s-triazine, 2-(p-bromophenyl)-4,6-bis(trichloromethyl)-s-triazine, 2-(p-tolyl)-4,6-bis(trichloromethyl)-s-triazine, 2-n-propyl-4,6-bis(trichloromethyl)-s-triazine, 2-(α,α,ß-trichloroethyl)-4,6-bis(trichloromethyl)-s-triazine, 2-styryl-4,6-bis(trichloromethyl)-s-triazine, 2-[2-(p-methoxyphenyl)ethenyl]-4,6-bis(trichloromethyl)-s-triazine, 2-[2-(o-methoxyphenyl)ethenyl]-4,6-bis(trichloromethyl)-s-triazine, 2-[2-(p-butoxyphenyl)ethenyl]-4,6-bis(trichloromethyl)-s-triazine, 2-[2-(3,4-dimethoxyphenyl)ethenyl]-4,6-bis(trichloromethyl)-s-triazine, 2-[2-(3,4,5-trimethoxyphenyl)ethenyl]-4,6-bis(trichloromethyl)-s-triazine, 2-(1-naphthyl)-4,6-bis(trichloromethyl)-s-triazine, 2-(4-biphenylyl)-4,6-bis(trichloromethyl)-s-triazine, 2-[2-{N,N-bis(2-hydroxyethyl)amino}ethoxy]-4,6-bis(trichloromethyl)-s-triazine, 2-[2-{N-hydroxyethyl-N-ethylamino}ethoxy]-4,6-bis(trichloromethyl)-s-triazine, 2-[2-{N-hydroxyethyl-N-methylamino}ethoxy]-4,6-bis(trichloromethyl)-s-triazine, and 2-[2-{N,N-diallylamino}ethoxy]-4,6-bis(trichloromethyl)-s-triazine.

Examples of the copper compound preferably used include copper acetylacetonate, copper(II) acetate, copper oleate, copper(II) chloride, and copper(II) bromide.

Examples of the tin compound include di-n-butyltin dimaleate, dimaleate, di-n-octyltin dilaurate, and di-n-butyltin dilaurate. Preferred are di-n-octyltin dilaurate and di-n-butyltin dilaurate.

The vanadium compound is preferably a compound of tetravalent and/or pentavalent vanadium. Examples of the compound of tetravalent and/or pentavalent vanadium include compounds described in JP 2003-096122 A, such as divanadium(IV) tetroxide, vanadium(IV) oxide acetylacetonate, vanadyl(IV) oxalate, vanadyl(IV) sulfate, oxobis(1-phenyl-1,3-butanedionato)vanadium(IV), bis(maltolato)oxovanadium(IV), vanadium(V) pentoxide, sodium metavanadate(V), and ammonium metavanadate(V).

Examples of the halogen compound preferably used include dilauryldimethylammonium chloride, lauryldimethylbenzylammonium chloride, benzyltrimethylammonium chloride, tetramethylammonium chloride, benzyldimethylcetylammonium chloride, and dilauryldimethylammonium bromide.

Examples of the aldehydes include terephthalaldehyde and benzaldehyde derivatives. Examples of the benzaldehyde derivative include dimethylaminobenzaldehyde, p-methyloxybenzaldehyde, p-ethyloxybenzaldehyde, and p-n-octyloxybenzaldehyde.

Among the examples of the polymerization accelerator (g), preferred are tertiary aliphatic amines, sulfinic acids, salts of sulfinic acids, sulfur-containing reducing inorganic compounds, copper compounds, and vanadium compounds. Among these, more preferred is at least one selected from the group consisting of; tertiary aliphatic amines such as N-methyldiethanolamine and triethanolamine; sulfinic acids such as sodium p-toluenesulfinate, sodium benzenesulfinate, and sodium 2,4,6-triisopropylbenzenesulfinate; sulfur-containing reducing inorganic compounds such as sodium sulfite, potassium sulfite, calcium sulfite, ammonium sulfite, sodium hydrogen sulfite, and potassium hydrogen sulfite; copper compounds such as copper acetylacetonate and copper(II) acetate; and vanadium compounds such as vanadium (IV) oxide acetylacetonate and bis(maltolato)oxovanadium (IV). When the dental cement of the present invention comprises the photopolymerization initiator (f), an aromatic tertiary amine having an electron withdrawing group, such as ethyl 4-(N,N-dimethylamino)benzoate, n-butoxyethyl 4-(N,N-dimethylamino)benzoate, or 4-(N,N-dimethylamino)benzophenone, is preferably used as the polymerization accelerator (g).

As the polymerization accelerator (g), one of these examples may be contained alone, or two or more thereof may be contained in combination. The content of the polymerization accelerator (g) is not particularly limited. In view of, for example, the curability of the resultant composition, the content of the polymerization accelerator (g) is preferably 0.01 to 20 parts by mass, more preferably 0.05 to 10 parts by mass, and most preferably 0.1 to 5 parts by mass, with respect to 100 parts by mass of the total polymerizable monomers.

The dental cement of the present invention may further comprise an amide proton-containing polyfunctional (meth)acrylamide polymerizable monomer (h) as a polymerizable monomer component. The polyfunctional (meth)acrylamide polymerizable monomer (h) containing at least one amide proton has high hydrophilicity owing to the at least one amide proton, penetrates easily into the collagen layer of dentin, and shows very high curability together with other components of the dental cement owing to a plurality of polymerizable groups per molecule. These contribute to higher bond strength to dentin.

Examples of the polyfunctional (meth)acrylamide polymerizable monomer (h) include a polyfunctional (meth)acrylamide polymerizable monomer (h1) represented by the following general formula (3), polyfunctional (meth)acrylamide polymerizable monomer (h2) represented by the following general formula (4), and polyfunctional (meth)acrylamide polymerizable monomer (h3) represented by the following general formula (5).

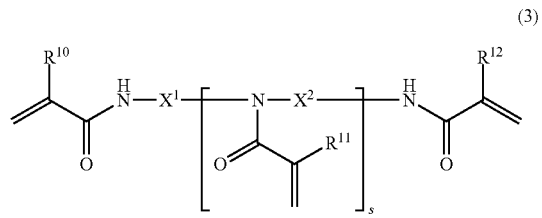

(3)

(In the formula, $R^{10}$, $R^{11}$, and $R^{12}$ are each independently a hydrogen atom or methyl group, s is an integer of 1 to 6, $X^1$ and $X^2$ are each independently an optionally substituted $C_1$ to $C_8$ linear or branched alkylene group.)

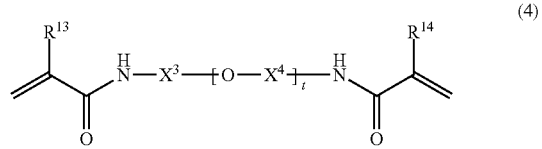

(4)

(In the formula, $R^{13}$ and $R^{14}$ are each independently a hydrogen atom or methyl group, t is 2 or 3, and $X^3$ and $X^4$ are each independently an optionally substituted $C_1$ to $C_8$ linear or branched alkylene group.)

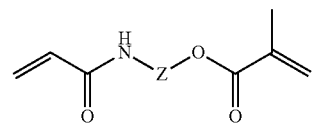

(5)

(In the formula, Z is an optionally substituted $C_1$ to $C_8$ linear or branched aliphatic or aromatic group, and the aliphatic group may be interrupted by at least one linking group selected from the group consisting of —O—, —S—, —CO—, —CO—O—, —O—CO—, —$NR^{15}$—, —CO—$NR^{15}$—, —$NR^{15}$—CO—, —CO—O—$NR^{15}$—, —O—CON$R^{15}$—, and —$NR^{15}$—CO—$NR^{15}$—. $R^{15}$ represents a hydrogen atom or optionally substituted $C_1$ to $C_8$ linear or branched aliphatic group.)

$R^{10}$, $R^{11}$, $R^{12}$, $R^{13}$, and $R^{14}$ are each preferably a hydrogen atom in view of adhesion to tooth structures and polymerization curability. s is preferably an integer of 1 to 4, more preferably an integer of 1 to 3, and particularly preferably 1 or 2. t is preferably 3.

Examples of the optionally substituted $C_1$ to $C_8$ linear or branched alkylene group represented by $X^1$, $X^2$, $X^3$, and $X^4$ include methylene, methylmethylene, ethylene, 1-methylethylene, 2-methylethylene, trimethylene, 1-ethylethylene, 2-ethylethylene, 1,2-dimethylethylene, 2,2-dimethylethylene, 1-methyltrimethylene, 2-methyltrimethylene, 3-methyltrimethylene, tetramethylene, 1-propylethylene, 2-propylethylene, 1-ethyl-1-methylethylene, 1-ethyl-2-methylethylene, 1,1,2-trimethylethylene, 1,2,2-trimethylethylene, 1-ethyltrimethylene, 2-ethyltrimethylene, 3-ethyltrimethylene, 1,1-dimethyltrimethylene, 1,2-dimethyltrimethylene, 1,3-dimethyltrimethylene, 2,3-dimethyltrimethylene, 3,3-dimethyltrimethylene, 1-methyltetramethylene, 2-methyltetramethylene, 3-methyltetramethylene, 4-methyltetramethylene, pentamethylene, 1-butylethylene, 2-butylethylene, 1-methyl-1-propylethylene, 1-methyl-2-propylethylene, 2-methyl-2-propylethylene, 1,1-diethylethylene, 1,2-diethylethylene, 2,2-diethylethylene, 1-ethyl-1,2-dimethylethylene, 1-ethyl-2,2-dimethylethylene, 1-methylpentamethylene, 2-methylpentamethylene, 3-methylpentamethylene, 4-methylpentamethylene, 5-methylpentamethylene, and hexamethylene groups.

Preferred examples of the substituent in $X^1$, $X^2$, $X^3$, and $X^4$ include a halogen atom (fluorine, chlorine, bromine, or iodine atom), carboxy group, hydroxy group, amino group, amino group mono- or di-substituted by a $C_1$ to $C_8$ alkyl group, acyl group, acyloxy group, amide group, $C_2$ to $C_8$ alkoxycarbonyl group, $C_1$ to $C_8$ alkoxy group, $C_1$ to $C_8$ alkylthio group, and $C_1$ to $C_8$ alkyl group, and more preferred examples include a halogen atom (fluorine, chlorine, bromine, or iodine atom) and $C_1$ to $C_8$ alkyl group. Example of the alkyl group include methyl, ethyl, n-propyl, isopropyl, n-butyl, isobutyl, sec-butyl, 2-methylpropyl, tert-butyl, n-pentyl, isopentyl, n-hexyl, n-heptyl, 2-methylhexyl, and n-octyl groups. The alkyl group is preferably a linear or branched $C_1$ to $C_4$ alkyl group. The number of the substituents is not particularly limited. The number of the/-substituents may be about 1 to 8, and is preferably 1, 2, or 3.

The optionally substituted $C_1$ to $C_8$ aliphatic group represented by Z may be a saturated aliphatic group (such as an alkylene group or cycloalkylene group (for example, 1,4-cyclohexylene group)) or unsaturated aliphatic group (such as an alkenylene group or alkynylene group), and is preferably a saturated aliphatic group (alkylene group) in view of availability, ease of production, and chemical stability. Z is preferably an optionally substituted, linear or branched $C_1$ to $C_4$ aliphatic group and more preferably an optionally substituted, linear or branched $C_2$ to $C_4$ aliphatic group in view of adhesion to tooth structures and polymerization curability. Examples of the $C_1$ to $C_8$ alkylene group are the same as those of $X^1$, $X^2$, $X^3$, and $X^4$.

Examples of the optionally substituted aromatic group represented by Z include an aryl group and aromatic heterocyclic group. As the aromatic group, an aryl group is more preferred than an aromatic heterocyclic group. The hetero ring of the aromatic heterocyclic group is generally unsaturated. The aromatic hetero ring is preferably a 5-membered or 6-membered ring. As the aryl group, for example, a phenyl group is preferred. Examples of the aromatic heterocyclic group include furan, thiophene, pyrrole, oxazole, isoxazole, thiazole, isothiazole, imidazole, pyrazole, furazan, triazole, pyran, pyridine, pyridazine, pyrimidine, pyrazine, and 1,3,5-triazine groups. Among these aromatic groups, a phenyl group is particularly preferred.

The aliphatic group represented by $R^{15}$ may be either a saturated aliphatic group (alkyl group) or unsaturated aliphatic group (alkenyl or alkynyl group), and is preferably a saturated aliphatic group (alkyl group) in view of availability, ease of production, and chemical stability. Examples of the alkyl group include $C_1$ to $C_8$ alkyl groups which are identical to those described as the substituents in $X^1$, $X^2$, $X^3$, and $X^4$. $R^{15}$ is more preferably a hydrogen atom or optionally substituted linear or branched $C_1$ to $C_4$ alkyl group and even more preferably a hydrogen atom or optionally substituted linear or branched $C_1$ to $C_3$ alkyl group.

The aliphatic group represented by Z may be interrupted by the at least one linking group described above. That is, the at least one linking group may be introduced into the aliphatic group. The number of the linking groups interrupting the aliphatic group represented by Z is not particularly limited, and may be about 1 to 10, preferably 1, 2, or 3, and more preferably 1 or 2. In the formula (5), the aliphatic group represented by Z is preferably not interrupted by two or more continuous linking groups. That is, the linking groups are preferably not adjacent to each other. The linking group is more preferably at least one linking group selected from the group consisting of —O—, —S—, —CO—, —CO—O—, —O—CO—, —NH—, —CO—NH—, —NH—CO—, —CO—O—NH—, —O—CO—NH—, and —NH—CO—NH— and even more preferably at least one linking group selected from the group consisting of —O—, —S—, —CO—, —NH—, —CO—NH—, and —NH—CO—.

Specific examples of the polyfunctional (meth)acrylamide polymerizable monomer (h1) represented by the formula (3) include, but are not particularly limited to, the following.

Compound (h1-1)

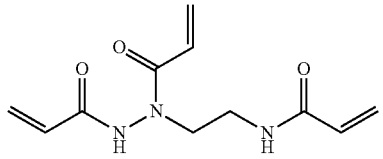

Compound (h1-2)

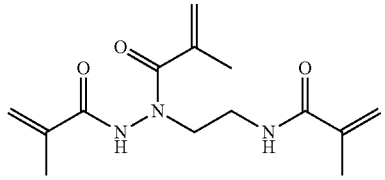

Compound (h1-3)

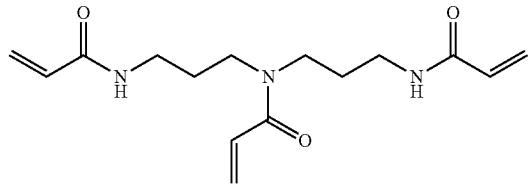

Compound (h1-4)

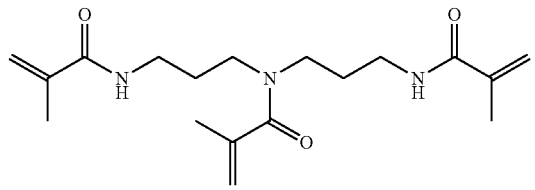

Compound (h1-5)

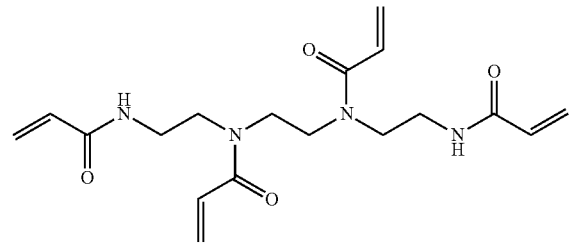 [SMILES: C=CC(=O)NCCN(CCN(CCNC(=O)C=C)C(=O)C=C)C(=O)C=C]

Compound (h1-6)

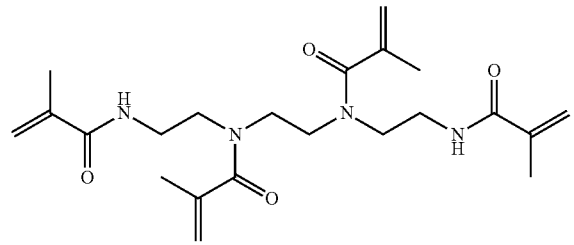

Compound (h1-7)

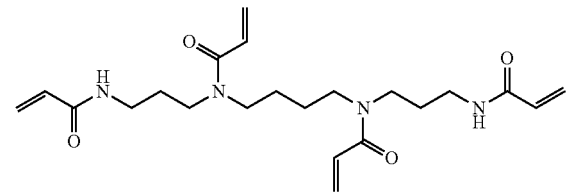

Compound (h1-8)

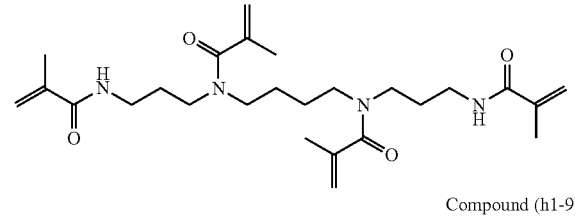

Compound (h1-9)

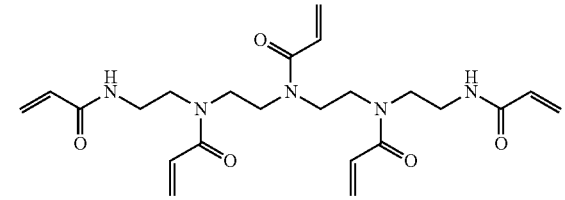

Compound (h1-10)

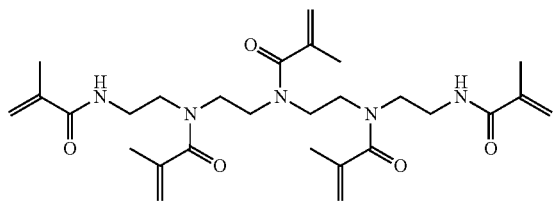

Compound (h1-11)

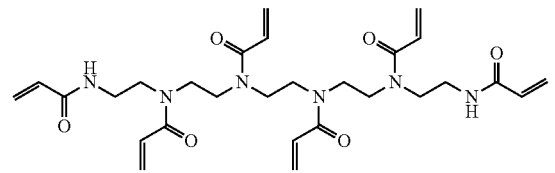

Compound (h1-12)

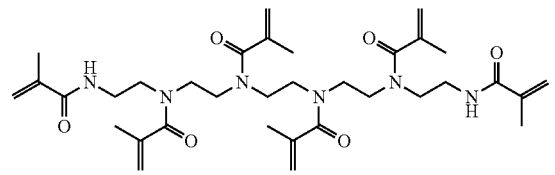

Among these, in view of adhesion to tooth structures and polymerization curability, the compound (h1-1), compound (h1-3), compound (h1-5), and compound (h1-7) are preferred, and the compound (h1-1) and compound (h1-5) are more preferred. The compound (h1-5) is most preferred because of its high hydrophilicity responsible for penetration into the collagen layer of dentin.

Specific examples of the polyfunctional (meth)acrylamide polymerizable monomer (h2) represented by the formula (4) include, but are not particularly limited to, the following.

Compound (h2-1)

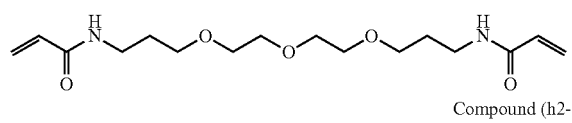

Compound (h2-2)

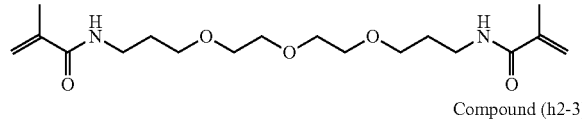

Compound (h2-3)

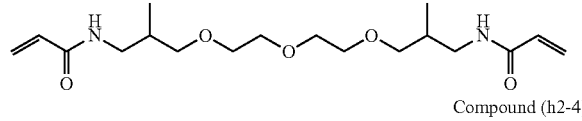

Compound (h2-4)

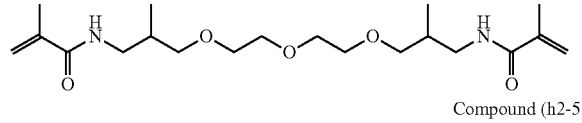

Compound (h2-5)

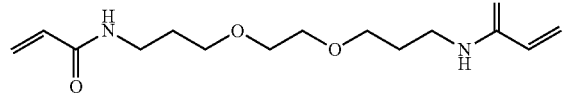

Compound (h2-6)

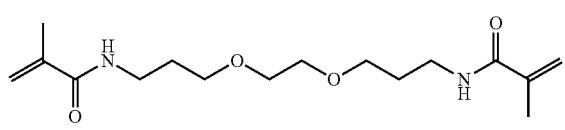

Compound (h2-7)

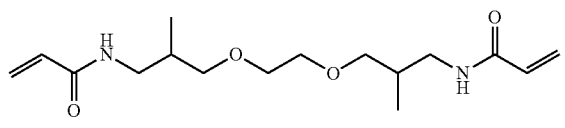

Compound (h2-8)

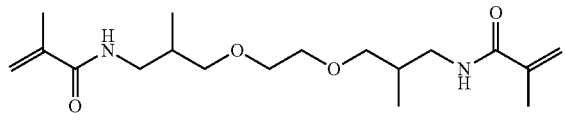

Compound (h2-9)

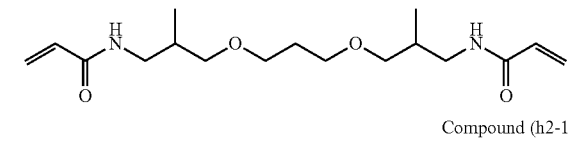

Compound (h2-10)

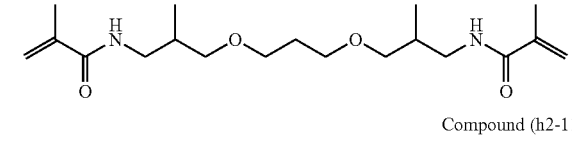

Compound (h2-11)

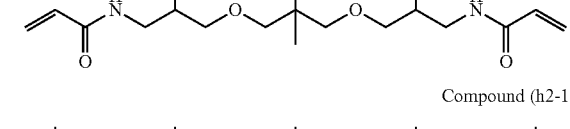

Compound (h2-12)

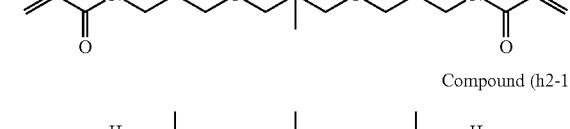

Compound (h2-13)

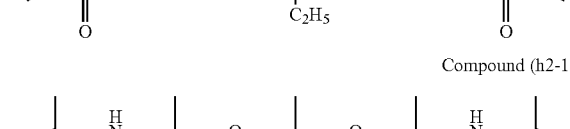

Compound (h2-14)

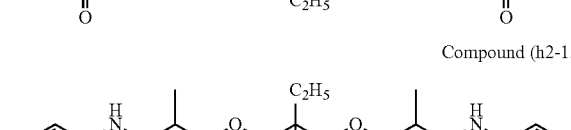

Compound (h2-15)

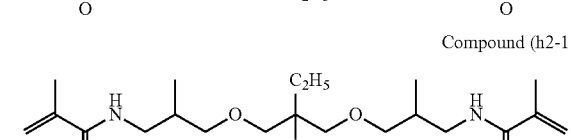

Compound (h2-16)

-continued

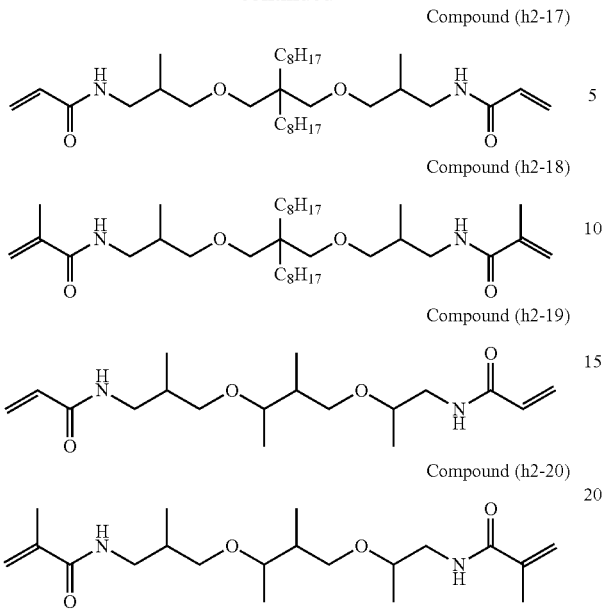

Among these, in view of adhesion to tooth structures and polymerization curability, the compound (h2-1), compound (h2-3), compound (h2-5), and compound (h2-7) are preferred, and the compound (h2-1) and compound (h2-3) are more preferred. The compound (h2-1) is most preferred because of its high hydrophilicity responsible for penetration into the collagen layer of dentin.

Specific examples of the polyfunctional (meth)acrylamide polymerizable monomer (h3) (which may hereinafter be referred to as an asymmetric polyfunctional (meth)acrylamide polymerizable monomer (h3)) represented by the formula (5) include, but are not particularly limited to, the following.

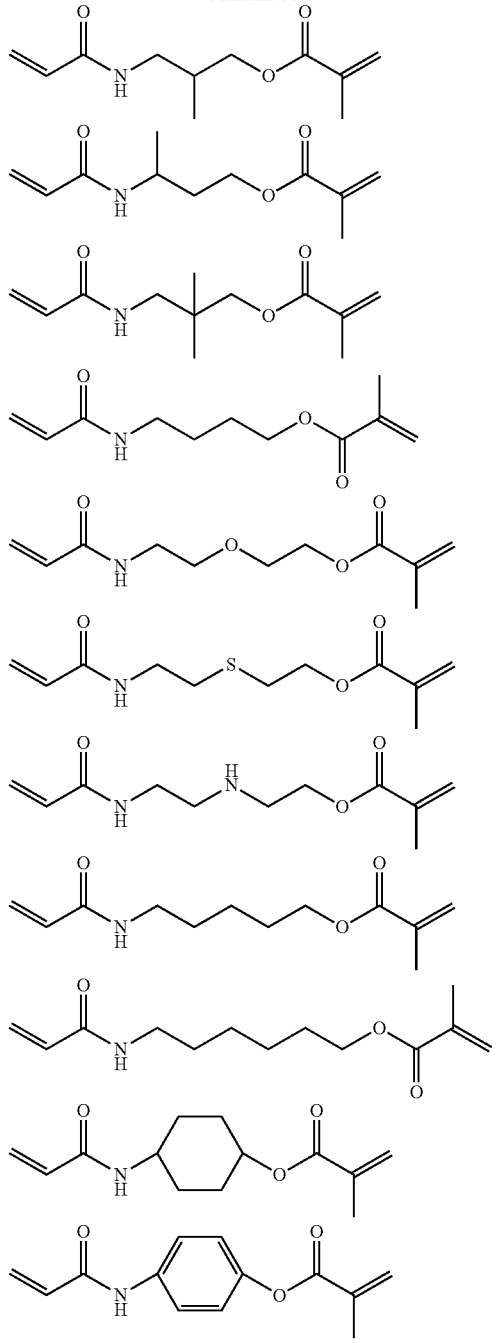

Among these, N-methacryloyloxyethyl acrylamide, N-methacryloyloxypropyl acrylamide, N-methacryloyloxybutyl acrylamide, N-(1-ethyl-(2-methacryloyloxy)ethyl) acrylamide, and N-(2-(2-methacryloyloxyethoxy)ethyl) acrylamide are more preferred in view of adhesion to tooth structures and polymerization curability. N-methacryloyloxyethyl acrylamide and N-methacryloyloxypropyl acrylamide are most preferred because of its high hydrophilicity responsible for penetration into the collagen layer of dentin.

As the polyfunctional (meth)acrylamide polymerizable monomer (h) containing at least one amide proton, one of these examples may be contained alone, or two or more thereof may be contained in combination. For example, the polyfunctional (meth)acrylamide polymerizable monomer (h3) and one or more polymerizable monomers selected from the group consisting of the polyfunctional (meth) acrylamide polymerizable monomer (h1) and polyfunctional (meth)acrylamide polymerizable monomer (h2) may be combined. The content of the polyfunctional (meth)acrylamide polymerizable monomer (h) is not particularly limited as long as the effect of the present invention can be obtained. The content of the polyfunctional (meth)acrylamide polymerizable monomer (h) is preferably in the range of 0.1 to 30 parts by mass, more preferably in the range of 0.5 to 25 parts by mass, and most preferably in the range of 1.0 to 20 parts by mass, in 100 parts by mass of the total polymerizable monomer components in the dental cement.

The dental cement of the present invention may further comprise or may not comprise a hydrophilic monofunctional polymerizable monomer (i) as a polymerizable monomer component. The hydrophilic monofunctional polymerizable monomer (i) refers to a monofunctional polymerizable monomer having a solubility of 5 mass % or more in water at 25° C. and being other than (a), (b), and (h). The solubility in water at 25° C. is preferably 10 mass % or more and more preferably 15 mass % or more. The addition of the hydrophilic monofunctional polymerizable monomer (i) achieves higher bond strength to dentin.

The hydrophilic monofunctional polymerizable monomer (i) has at least one hydrophilic group such as hydroxy, oxymethylene, oxyethylene, oxypropylene, and amide groups. Examples of the hydrophilic monofunctional polymerizable monomer (i) include: hydrophilic monofunctional (meth)acrylate polymerizable monomers such as 2-hydroxyethyl (meth)acrylate, 3-hydroxypropyl (meth)acrylate, 2-hydroxypropyl (meth)acrylate, 1,3-dihydroxypropyl (meth)acrylate, 2,3-dihydroxypropyl (meth)acrylate, and 2-trimethylammoniumethyl (meth)acrylchloride; and hydrophilic monofunctional (meth)acrylamide polymerizable monomers such as N-methylol (meth)acrylamide, N-hydroxyethyl (meth)acrylamide, N,N-bis(2-dihydroxyethyl) (meth)acrylamide, N-methoxymethyl (meth)acrylamide, N-ethoxymethyl (meth)acrylamide, diacetone (meth)acrylamide, 4-(meth)acryloylmorpholine, N-trihydroxymethyl-N-methyl (meth)acrylamide, and monofunctional (meth) acrylamide polymerizable monomers represented by the following general formula (6).

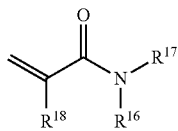

(6)

(In the formula, $R^{16}$ and $R^{17}$ are each independently an optionally substituted, linear or branched $C_1$ to $C_3$ alkyl group, and $R^{18}$ is a hydrogen atom or methyl group.)

Examples of the substituent in $R^{16}$ and $R^{17}$ are the same as those in $X^1$, $X^2$, $X^3$, and $X^4$. Examples of the $C_1$ to $C_3$ alkyl group represented by $R^{16}$ and $R^{17}$ include methyl, ethyl, n-propyl, and isopropyl groups.

Among these examples of the hydrophilic monofunctional polymerizable monomer (i), in view of adhesion to tooth structures, 2-hydroxyethyl (meth)acrylate, 2,3-dihydroxypropyl (meth)acrylate, diacetone (meth)acrylamide, and the hydrophilic monofunctional (meth)acrylamide polymerizable monomers represented by the general formula (6) are preferred, and the monofunctional (meth) acrylamide polymerizable monomers represented by the general formula (6) are more preferred. As the hydrophilic monofunctional polymerizable monomer (i), one of the above monomers may be used alone, or two or more thereof may be used in combination.

Among the monofunctional (meth)acrylamide polymerizable monomers represented by the general formula (6), N,N-dimethylacrylamide and N,N-diethylacrylamide are more preferred, and N,N-diethylacrylamide is most preferred, in view of storage stability.

The content of the hydrophilic monofunctional polymerizable monomer (i) of the present invention is not particularly limited as long as the effect of the present invention can be obtained. In order to obtain a sufficient effect on improvement of the bond strength and sufficient mechanical strength, the content of the hydrophilic monofunctional polymerizable monomer (i) is preferably in the range of 1 to 30 parts by mass, more preferably in the range of 1 to 25 parts by mass, even more preferably in the range of 2 to 20 parts by mass, and particularly preferably in the range of 2 to 10 parts by mass, in 100 parts by mass of the total polymerizable monomer components in the dental cement.

As long as the effect of the present invention can be obtained, the dental cement of the present invention may comprise a polymerizable monomer (j) in addition to the acid group-containing (meth)acrylic polymerizable monomer (a), polyfunctional (meth)acrylic polymerizable monomer (b) containing no acid group, amide proton-containing polyfunctional (meth)acrylamide polymerizable monomer (h), and hydrophilic monofunctional polymerizable monomer (i) in order to improve the bond strength, handling properties, and mechanical strength. Examples of the polymerizable monomer (j) include a hydrophilic polyfunctional (meth)acrylate polymerizable monomer (j1) and/or symmetric (meth)acrylamide compound (j2). The hydrophilic polyfunctional (meth)acrylate polymerizable monomer 01) refers to a polyfunctional polymerizable monomer having a solubility of 5 mass % or more in water at 25° C. and being other than (a), (b), and (h). The solubility in water at 25° C. is preferably 10 mass % or more and more preferably 15 mass % or more. Examples of the hydrophilic polyfunctional (meth)acrylate polymeriszable monomer (j1) include pentaerythritol di(meth)acrylate, erythritol di(meth)acrylate, mannitol di(meth)acrylate, xylitol di(meth)acrylate, sorbitol di(meth)acrylate, and glycerol di(meth)acrylate. Examples of the symmetric (meth)acrylamide compound (j2) include N,N'-ethylenebisacrylamide and N,N'-diethyl-1,3-propylene-bisacrylamide. As the polymerizable monomer 0), one of these examples may be used alone, or two or more thereof may be used in combination.

The dental cement of the present invention may further comprise a fluorine ion-releasing material. The addition of the fluorine ion-releasing material to the dental cement can provide acid resistance to tooth structures. Examples of the fluorine ion-releasing material include metal fluorides such as sodium fluoride, potassium fluoride, sodium monofluorophosphate, lithium fluoride, and ytterbium fluoride. One of these fluorine ion-releasing materials may be used alone, or two or more thereof may be used in combination.

Preferred embodiments of the multi-part dental cement of the present invention are as follows.

1) A multi-part dental cement comprising a first paste and second paste, wherein the first paste comprises the acid group-containing (meth)acrylic polymerizable monomer (a), polyfunctional (meth)acrylic polymerizable monomer (b) containing no acid group, chemical polymerization initiator (c-1), filler (d), and photopolymerization initiator (0, and the second paste comprises the polyfunctional (meth)acrylic polymerizable monomer (b) containing no acid group, chemical polymerization initiator (c-2), and filler (e).

2) A multi-part dental cement comprising a first paste and second paste, wherein the first paste comprises the acid group-containing (meth)acrylic polymerizable monomer (a), polyfunctional (meth)acrylic polymerizable monomer (b) containing no acid group, chemical polymerization initiator (c-1), filler (d), and photopolymerization initiator (f), and the second paste comprises the polyfunctional (meth)acrylic polymerizable monomer (b) containing no acid group, chemical polymerization initiator (c-2), filler (e), and polymerization accelerator (g).

3) A multi-part dental cement comprising a first paste and second paste, wherein the first paste comprises the acid group-containing (meth)acrylic polymerizable monomer (a), polyfunctional (meth)acrylic polymerizable monomer (b) containing no acid group, chemical polymerization initiator (c-1), filler (d), and filler (e), and the second paste comprises the polyfunctional (meth)acrylic polymerizable monomer (b) containing no acid group, chemical polymerization initiator (c-2), and filler (e).

4) A multi-part dental cement comprising a first paste and second paste, wherein the first paste comprises the acid group-containing (meth)acrylic polymerizable monomer (a), polyfunctional (meth)acrylic polymerizable monomer (b) containing no acid group, chemical polymerization initiator (c-1), filler (d), filler (e), and photopolymerization initiator (f), and the second paste comprises the polyfunctional (meth)acrylic polymerizable monomer (b) containing no acid group, chemical polymerization initiator (c-2), and filler (e).

5) A multi-part dental cement comprising a first paste and second paste, wherein the first paste comprises the acid group-containing (meth)acrylic polymerizable monomer (a), polyfunctional (meth)acrylic polymerizable monomer (b) containing no acid group, chemical polymerization initiator (c-1), filler (d), filler (e), and photopolymerization initiator (f), and the second paste comprises the polyfunctional (meth)acrylic polymerizable monomer (b) containing no acid group, chemical polymerization initiator (c-2), filler (e), and polymerization accelerator (g).

6) A multi-part dental cement comprising a first paste and second paste, wherein the first paste comprises the acid group-containing (meth)acrylic polymerizable monomer (a), polyfunctional (meth)acrylic polymerizable monomer (b) containing no acid group, hydrophilic monofunctional polymerizable monomer (i), chemical polymerization initiator (c-1), filler (d), and photopolymerization initiator (f), and the second paste comprises the poly-functional (meth)acrylic polymerizable monomer (b) containing no acid group, chemical polymerization initiator (c-2), and filler (e).

7) A multi-part dental cement comprising a first paste and second paste, wherein the first paste comprises the acid group-containing (meth)acrylic polymerizable monomer (a), polyfunctional (meth)acrylic polymerizable monomer (b) containing no acid group, hydrophilic monofunctional polymerizable monomer (i), chemical polymerization initiator (c-1), filler (d), and photopolymerization initiator (f), and the second paste comprises the polyfunctional (meth)acrylic polymerizable monomer (b) containing no acid group, chemical polymerization initiator (c-2), filler (e), and polymerization accelerator (g).

8) A multi-part dental cement comprising a first paste and second paste, wherein the first paste comprises the acid group-containing (meth)acrylic polymerizable monomer (a), polyfunctional (meth)acrylic polymerizable monomer (b) containing no acid group, hydrophilic monofunctional polymerizable monomer (i), chemical polymerization initiator (c-1), filler (d), filler (e), and photopolymerization initiator (f), and the second paste comprises the polyfunctional (meth)acrylic polymerizable monomer (b) containing no acid group, chemical polymerization initiator (c-2), filler (e), and polymerization accelerator (g).

9) A multi-part dental cement comprising a first paste and second paste, wherein the first paste comprises the acid group-containing (meth)acrylic polymerizable monomer (a), polyfunctional (meth)acrylic polymerizable monomer (b) containing no acid group, amide proton-containing polyfunctional (meth)acrylamide polymerizable monomer (h), chemical polymerization initiator (c-1), filler (d), and photopolymerization initiator (f), and the second paste comprises the polyfunctional (meth)acrylic polymerizable monomer (b) containing no acid group, chemical polymerization initiator (c-2), and filler (e).

10) A multi-part dental cement comprising a first paste and second paste, wherein the first paste comprises the acid group-containing (meth)acrylic polymerizable monomer (a), polyfunctional (meth)acrylic polymerizable monomer (b) containing no acid group, amide proton-containing polyfunctional (meth)acrylamide polymerizable monomer (h), chemical polymerization initiator (c-1), filler (d), and photopolymerization initiator (f), and the second paste comprises the polyfunctional (meth)acrylic polymerizable monomer (b) containing no acid group, chemical polymerization initiator (c-2), filler (e), and polymerization accelerator (g).

11) A multi-part dental cement comprising a first paste and second paste, wherein the first paste comprises the acid group-containing (meth)acrylic polymerizable monomer (a), polyfunctional (meth)acrylic polymerizable monomer (b) containing no acid group, amide proton-containing polyfunctional (meth)acrylamide polymerizable monomer (h), chemical polymerization initiator (c-1), filler (d), filler (e), and photopolymerization initiator (0, and the second paste comprises the polyfunctional (meth)acrylic polymerizable monomer (b) containing no acid group, chemical polymerization initiator (c-2), filler (e), and polymerization accelerator (g).

In any of the above preferred embodiments, appropriate adjustment of the contents of the components, appropriate selection of the types of the compounds, and addition or omission of the optional components (for example, the polymerization accelerator (g), photopolymerization initiator (f), and polymerization inhibitor) can be done on the basis of the foregoing description. In any of the above preferred embodiments, when the first paste comprises the filler (d) and filler (e), the filler (e) may be surface-treated with the organosilazane (B) alone, but is preferably not surface-treated with the organosilazane (B).

Furthermore, for example, a pH adjuster, polymerization inhibitor, ultraviolet absorber, thickener, colorant, antibacterial agent, and flavor may be added to the multi-part dental cement of the present invention as long as the effect of the present invention is not impaired.

The present invention encompasses embodiments obtainable by combining the above features in various manners within the technical scope of the present invention as long as the effect of the present invention can be obtained.

EXAMPLES

Hereinafter, the present invention will be described in detail by way of examples and comparative examples. The present invention is not limited by these examples. Abbreviations used hereinafter are as follows. Except for compounds for which synthesis methods are specifically described, compounds used in the following examples and comparative examples are commercially-available products.

[Acid group-containing (meth)acrylic polymerizable monomer (a)]
MDP: 10-methacryloyloxydecyl dihydrogen phosphate
4-META: 4-[2-(methacryloyloxy)ethoxycarbonyl]phthalic acid anhydride

[Polyfunctional (meth)acrylic polymerizable monomer (b) containing no acid group]
Bis-GMA: 2,2-bis[4-(3-methacryloyloxy-2-hydroxypropoxy)phenyl]propane
D-2.6E: 2,2-bis(4-methacryloyloxypolyethoxyphenyl)propane (having an average number of moles of added ethoxy groups of 2.6)
TEGDMA: Triethylene glycol dimethacrylate

[Chemical polymerization initiator (c)]
Oxidizing agent (c-1)
THP: 1,1,3,3-tetramethylbutyl hydroperoxide
BPO: benzoyl peroxide
Reducing agent (c-2)
DMETU: 4,4-dimethyl-2-imidazolidinethione
TMTU 1,1,3-trimethylthiourea
DEPT: N,N-bis(2-hydroxyethyl)-p-toluidine

[Filler (e)]
Surface-Treated Silica: Silane-Treated Silica Powder
Silica powder (manufactured by Nitchitsu Co., Ltd. under the trade name of Hi-Silica) was ground in a ball mill to obtain a pulverized silica powder. The pulverized silica powder thus obtained was measured using a laser diffraction particle size distribution analyzer (model "SALD-2100" manufactured by Shimadzu Corporation) to obtain the average particle diameter, which was 2.2 μm By a conventional method, 100 parts by mass of this pulverized silica powder was surface-treated with 4 parts by mass of 3-methacryloyloxypropyltrimethoxysilane. Surface-treated silica was thus obtained.

Surface-Treated Ba Glass Powder: Silane-Treated Ba Glass Powder
Barium glass (product code "E-3000" manufactured by Esstech, Inc.) was ground in a ball mill to obtain a barium glass powder. The barium glass powder thus obtained was measured using a laser diffraction particle size distribution analyzer (model "SALD-2100" manufactured by Shimadzu Corporation) to obtain the average particle diameter, which was 2.4 μm. By a conventional method, 100 parts by mass of this barium glass powder was surface-treated with 3 parts by mass of 3-methacryloyloxypropyltrimethoxysilane. A surface-treated Ba glass powder was thus obtained.

SiO$_2$-Coated YBF: Silica-Coated Ytterbium Fluoride
A commercially-available product (SG-YBF100WSCMP10; average particle diameter: 110 nm; spherical shape; manufacturer: Sukgyung AT Co., Ltd.) was used as it is.

Spherical Nanosilica: Silane-Treated Colloidal Silica Powder
A commercially-available product (Sciqas (treated with methacrylsilane); average particle diameter: 50 nm; manufacturer: SAKAI CHEMICAL INDUSTRY CO., LTD.) was used as it is.

Fumed Silica: Silan-Treated Colloidal Silica Powder
To 100 parts by mass of distilled water were added 0.3 parts by mass of acetic acid and 3 parts by mass of 3-methacryloyloxypropyltrimethoxysilane, and the resultant mixture was stirred. An amount of 50 parts by mass of a colloidal silica powder (manufactured by Nippon Aerosil Co., Ltd. under the trade name of AEROSIL OX 50 and having an average particle diameter of about 40 nm) was further added, and the resultant mixture was stirred for 1 hour. Water was removed by freeze-drying, followed by heat treatment at 80° C. for 5 hours to obtain a silane-treated colloidal silica powder.

[Photopolymerization Initiator (f)]
CQ: Dl-camphorquinone

[Polymerization Accelerator (g)]
DABE: Ethyl 4-(N,N-dimethylamino)benzoate
TPBSS: Sodium 2,4,6-triisopropylbenzenesulfinate
Na$_2$SO$_3$: Sodium sulfite

[Amide Proton-Containing Polyfunctional (Meth)Acrylamide Polymerizable Monomer (h)]
TAC4: N,N',N'',N'''-tetraacryloyltriethylenetetramine (compound (h1-5) represented by the following formula):

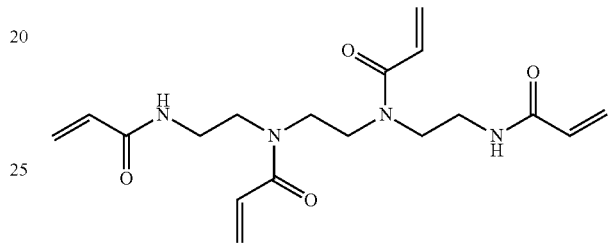

MAEA: N-methacryloyloxyethyl acrylamide (asymmetric polyfunctional (meth)acrylamide polymerizable monomer represented by the following formula):

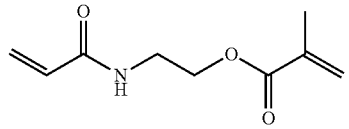

[Hydrophilic monofunctional polymerizable monomer (i)]
DEAA: N,N-diethylacrylamide
HEMA: 2-hydroxyethyl methacrylate

[Others]
BHT: 2,6-di-t-butyl-4-methylphenol (stabilizer (polymerization inhibitor))

Production Example 1

Production of filler (d-1)
As silica particles, SNOWTEX OL (manufactured by Nissan Chemical Industries, Ltd., having an average particle diameter of 50 nm, dispersed in water, and having a solid content concentration of 20%), which is a type of colloidal silica, was provided. As alcohol, isopropanol was provided. As the silane coupling agent (A), 3-methacryloyloxypropyltrimethoxysilane (KBM-503 manufactured by Shin-Etsu Chemical Co., Ltd.) was provided. As the organosilazane (B), 1,1,1,3,3,3-hexamethyldisilazane (HMDS, HDMS-1 manufactured by Shin-Etsu Chemical Co., Ltd.) was provided. An amount of 60 parts by mass of isopropanol was added to 100 parts by mass of a slurry containing the silica particles dispersed at a concentration of 20 mass % in water. The resultant mixture was mixed at room temperature (about 25° C.) to obtain a dispersion containing the silica particles dispersed in a liquid medium. To the dispersion were added 0.48 parts by mass of 3-methacryloyloxypropyltrimethoxysilane and 0.01 parts by mass of a polymerization inhibitor (3,5-dibutyl-4-hydroxytoluene (BHT) manufactured by KANTO CHEMICAL CO., INC.), and the resultant mixture was mixed at 40° C. for 72 hours. A hydroxy group existing on the surface of the silica particles was surface-treated with the silane coupling agent (A) in this step. Here, 3-methacryloyloxypropyltrimethoxysilane was added so that the surface of a necessary amount (a portion) of the hydroxy group would remain untreated. Next, 0.78 parts by mass of 1,1,1,3,3,3-hexamethyldisilazane was added to the mixture, and the resultant mixture was left at 40° C. for 72 hours. The silica particles were surface-treated in this step, and thus a silica particle material was obtained. Along with the progress of the surface treatment, the silica particles became hydrophobic and unable to stably exist in water and isopropanol, and therefore underwent aggregation and precipitation. In the surface treatment agent, the molar ratio between 3-methacryloyloxypropyltrimethoxysilane and hexamethyldisilazane was 2:5. To the total amount of the mixture obtained after the surface treatment was added 2.6 parts by mass of a 35% aqueous solution of hydrochloric acid to precipitate the silica particle material. The precipitate was collected by filtration using a filter paper (5A manufactured by Advantec Toyo Kaisha, Ltd.). The filtration residue (solids) was washed with pure water and then vacuum-dried at 100° C. to obtain a filler (d-1).

Production Example 2

Production of filler (d-2)

A filler (d-2) was produced in exactly the same manner as the method for synthesizing the filler (d-1), except that the content of 1,1,1,3,3,3-hexamethyldisilazane was 2.8 parts by mass. In the surface treatment agent, the molar ratio between 3-methacryloyloxypropyltrimethoxysilane and hexamethyldisilazane was 2:18.

Production Example 3

Synthesis of TAC4

In a 1-liter four-necked flask were put 21.9 g (0.15 mol) of triethylenetetramine (manufactured by Tokyo Chemical Industry Co., Ltd.), 75.9 g (0.75 mol) of triethylamine, 3.7 mg (0.03 mmol) of p-methoxyphenol, and 250 mL of dichloromethane, which were stirred and cooled to an internal temperature of 2° C. An amount of 100 mL of a dichloromethane solution of acrylic acid chloride (67.9 g, 0.75 mol) was added dropwise at 5° C. or lower over 2 hours. After the dropwise addition of the solution, the resultant mixture was stirred for 24 hours under the conditions of room temperature. The resultant reaction solution was filtered, and insoluble matters were washed with dichloromethane, and concentration was performed at 35° C. or lower under reduced pressure. The concentrated residue thus obtained was purified by silica gel column chromatography (developing solvent having a ratio of ethyl acetate:methanol=4:1). After the column purification, the solvent was removed under reduced pressure using a rotary evaporator to obtain a white solid. The solid was subjected to LC-MS analysis and $^1$H-NMR measurement. It was determined from the locations and integrals of signals that the white solid obtained was a target compound. The weight yield was 12.7 g, and the percentage yield was 23.3%.

MS m/z: 363 (M+H)$^+$
$^1$H-NMR (270 MHz D$_2$O): δ3.37 (m, 6H), 3.57 (m, 6H), 5.66 (m, 4H), 6.07 (m, 6H), 6.56 (m, 2H) (ppm)

Production Example 4

Synthesis of MAEA

In a 10-liter four-necked flask were put 172.7 g (1.5 mol) of hydroxyethyl acrylamide (manufactured by Kohjin Film & Chemicals Co., Ltd.), 167 g (1.65 mol) of triethylamine, 38 mg (0.3 mmol) of p-methoxyphenol, and 1500 mL of anhydrous tetrahydrofuran, which were stirred and cooled to an internal temperature of −10° C. An amount of 700 mL of an anhydrous tetrahydrofuran solution of methacrylic acid chloride (172.5 g, 1.65 mol) was added dropwise at 5° C. or lower over 2 hours. After the dropwise addition of the solution, the resultant mixture was stirred for 24 hours under the conditions of room temperature. The resultant reaction solution was filtered, and insoluble matters were washed with ethyl acetate. The filtrate was concentrated under reduced pressure, and the residue was dissolved in ethyl acetate. The resultant solution was filtered with Celite to remove a small amount of insoluble matters, and then the filtrate was washed with a mixture of saturated saline solution and purified water (1:1). The organic layer was dried with anhydrous sodium sulfate, and concentration was performed at 35° C. or lower under reduced pressure. The concentrated residue thus obtained was purified by silica gel column chromatography (developing solvent: ethyl acetate). After the column purification, the solvent was removed under reduced pressure using a rotary evaporator to obtain a pale yellow liquid. The liquid was subjected to LC-MS analysis and $^1$H-NMR measurement. It was determined from the locations and integrals of signals that the pale yellow liquid thus obtained was a target compound. The weight yield was 201.2 g, and the percentage yield was 73.3%.

MS m/z: 184 (M+H)$^+$
$^1$H-NMR (270 MHz CDCl$_3$): δ1.94 (m, 3H), 3.62 (m, 2H), 4.28 (m, 2H), 5.58 (m, 1H), 5.66 (m, 1H), 6.08 (s, 1H), 6.10 (m, 1H), 6.11 (m, 1H), 6.28 (m, 1H) (ppm)

Examples 1 to 16 and Comparative Examples 1 to 6

Using the materials, for example, those prepared in the above production examples, dental cements of Examples 1 to 16 and Comparative Examples 1 to 6 were each prepared as a paste by mixing all the components, other than the filler (d) or (e) (powder), specified in Table 1, 2, or 3 at ordinary temperature to obtain a homogeneous liquid component and mixing the homogeneous liquid component thus obtained and filler (d) or (e) (powder). Next, the consistency, discharging properties, and runniness were measured using these dental cements by the following methods. Tables 1 to 3 show the contents (parts by mass) of the components of these dental cements and the test results thereof.

[Consistency of dental cement]

After defoamed under vacuum, each of the prepared dental cements of Examples and Comparative Examples was loaded into a double-syringe (product number: ML2.5-08-S) manufactured by MIXPAC and allowed to stand at 25° C. for 2 hours. A sample for the consistency test was thus prepared. A static mixer was attached to the syringe. A piston was pushed in to push out 0.5 mL of the sample, which was allowed to stand on the center of a glass sheet (5 cm×5 cm) in the shape of a mound in a thermostatic chamber set at 25° C. (humidity: 40%). A 40 g glass sheet (5 cm×5 cm) was placed on the sample, and after 120 seconds, the longest diameter and shortest diameter of the sample were measured over the glass sheet. The arithmetic average of the two diameters was calculated and employed as the consistency (mm). The longest diameter of the sample refers to the longest one of the diameters that pass through the center of the sample, and the shortest diameter of the sample refers to one of the diameters that pass through the center of the sample, the one orthogonal to the longest diameter of the sample. Separately, after defoamed under vacuum, loaded into a double-syringe (product number: ML2.5-08-S) manufactured by MIXPAC, and allowed to stand in a thermostat set at 60° C. for 4 weeks, each of the dental cements was measured in the above-described manner. The resultant value was employed as the consistency measured after the 4-week storage at 60° C.

[Discharging properties of dental cement]

Each of the dental cements (4 g) prepared as pastes in Examples and Comparative Examples was loaded into a syringe container manufactured by MIXPAC, and a static mixer and piston were attached to the syringe. The syringe container was set up vertically in a universal testing machine (manufactured by Shimadzu Corporation under the product cord "AGI-100"). A crosshead fitted with a jig for a compressive strength test was moved downward on the piston attached to the syringe at a rate of 4 mm/minute to apply a load to the paste and discharge the paste from the opening of the syringe. The maximum load obtained then was employed as the discharge force. The measurement of the discharge force was performed at 25° C. When the discharge force is 40 N or less, discharge is easy and the discharging properties are good. When the discharge force is 40 N to 60 N, discharge is possible but the discharging properties are poor. When the discharge force is 60 N or more, discharge is difficult and the discharging properties are poor. Separately, after the dental cement as a paste was defoamed under vacuum, loaded into a double-syringe (product number: ML2.5-08-S) manufactured by MIXPAC, and then allowed to stand in a thermostat set at 60° C. for 4 weeks, the dental cement was measured in the above-described manner and the measured value was employed as the discharge force measured after the 4-week storage at 60° C.

[Runniness of dental cement]

Each of the dental cements prepared in Examples and Comparative Examples was loaded into a double-syringe (product number: ML2.5-08-S) manufactured by MIXPAC, and a static mixer and piston were attached to the syringe. A circle of 3 mm diameter was drawn on a dental mixing pad of 59 mm long and 83 mm wide. An amount of 30 mg of the dental cement was pushed out into the circle. The dental mixing pad was stood vertically in a thermostat set at 37 C° and left untouched for 3 minutes to measure how far the polymerizable composition moved away from the circle. This test was performed three times to obtain measured values, the average of which was employed as the runniness (mm). A dental cement having greater runniness is runnier. The runniness is preferably 3 mm or less and more preferably 2 mm or less.

Separately, after defoamed under vacuum, loaded into a double-syringe (product number: ML2.5-08-S) manufactured by MIXPAC, and then allowed to stand in a thermostat set at 60° C. for 4 weeks, the dental cement was measured in the above-described manner and the measured value was employed as the runniness measured after the 4-week storage at 60° C.

TABLE 1

| Component (parts by mass) | | Example 1 A | Example 1 B | Example 2 A | Example 2 B | Example 3 A | Example 3 B | Example 4 A | Example 4 B | Example 5 A | Example 5 B | Example 6 A | Example 6 B | Example 7 A | Example 7 B | Example 8 A | Example 8 B |
|---|---|---|---|---|---|---|---|---|---|---|---|---|---|---|---|---|---|
| Acid group-containing (meth)acrylic polymerizable monomer (a) | MDP | 10 | | 10 | | 10 | | 10 | | 10 | | 10 | | 10 | | 20 | |
| | 4-META | | | | | | | | | | | | | | | | |
| Polyfunctional (meth)acrylic polymerizable monomer (b) containing no acid group | Bis-GMA | 25 | | 25 | | 25 | | 25 | | 25 | | 25 | | 25 | | 25 | |
| | D-2.6E | 35 | | 35 | | 35 | | 35 | | 35 | | 35 | | 35 | | 35 | |
| | TEGDMA | 30 | | 30 | | 30 | | 30 | | 30 | | 30 | | 30 | | 30 | |
| Amide proton-containing polyfunctional (meth)acrylamide polymerizable monomer (h) | MAEA | | | | | | | | | | | | | | | | |
| | TAC4 | | | | | | | | | | | | | | | | |
| | DEAA | | | | | | | | | | | | | | | | |
| Hydrophilic monofunctional polymerizable monomer (i) | HEMA | | | | | | | | | | | | | | | | |
| Chemical polymerization initiator (c-1) | THP | 3 | | 3 | | 3 | | 3 | | 3 | | 3 | | 3 | | 3 | |
| | BPO | | 1 | | 1 | | 1 | | 1 | | 1 | | 1 | | 1 | | 1 |
| Chemical polymerization initiator (c-2) | DMETU | | | | | | | | | | | | | | | | |
| | TMTU | | | | | | | | | | | | | | | | |
| | DEPT | | | | | | | | | | | | | | | | |
| Photopolymerization initiator (f) | CQ | 0.1 | | 0.1 | | 0.1 | | 0.1 | | 0.1 | | 0.1 | | 0.1 | | 0.1 | |
| Polymerization accelerator (g) | DABE | | | | | | | | | | | | | | | | |
| | TPBSS | | | | | | | | | | | | | | | | |
| | Na$_2$SO$_3$ | | | | | | | | | | | | | | | | |
| Polymerization inhibitor | BHT | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 |
| Filler (d) | Filler (d-1) | 140 | | 140 | | 140 | | 140 | | | | 185 | | 140 | | 140 | |
| | Filler (d-2) | | | | | | | | | 140 | | | | | | | |
| Filler (e) | Surface-treated silica | | | | | | | | | 45 | | | | | | | |
| | Surface-treated Ba glass powder | 45 | 140 | 45 | 140 | 45 | 140 | 45 | 140 | | 140 | | 140 | 45 | 140 | | 140 |
| | SiO$_2$-coated YBF | | 45 | | 45 | | 45 | | 45 | | 45 | | 45 | | 45 | 45 | 45 |
| | Spherical nanosilica | | | | | | | | | | | | | | | | |
| | Fumed silica | | | | | | | | | | | | | | | | |
| Consistency measured just after preparation (mm) | | 27.0 | 28.5 | 26.9 | 28.5 | 28.1 | 29.2 | 27.7 | 28.3 | 29.2 | 30.9 | 24.9 | 25.1 | 26.7 | 27.3 | 26.4 | 27.2 |
| Consistency measured after 4-week storage at 60° C. (mm) | | 28.5 | | | | | | | | | | | | | | | |
| Difference between consistency measured just after preparation and consistency measured after 4-week storage at 60° C. (mm) | | 1.5 | | 1.6 | | 1.1 | | 0.6 | | 1.7 | | 0.2 | | 0.6 | | 0.8 | |
| Discharging properties of paste measured just after preparation (N) | | 30.2 | 32.5 | 30.5 | 32.9 | 31.5 | 32.6 | 30.4 | 32.8 | 32.3 | 33.4 | 37.9 | 38.4 | 33.2 | 35.8 | 33.3 | 35.1 |
| Discharging properties of paste measured after 4-week storage at 60° C. (N) | | | | | | | | | | | | | | | | | |
| Difference between discharging properties of paste measured just after preparation and discharging properties of paste measured after 4-week storage at 60° C. (N) | | 2.3 | | 2.4 | | 1.1 | | 2.4 | | 1.1 | | 0.5 | | 2.6 | | 1.8 | |
| Runniness measured just after preparation (mm) | | 0.0 | 0.0 | 0.0 | 0.0 | 0.0 | 0.0 | 0.0 | 0.0 | 0.1 | 0.1 | 0.0 | 0.0 | 0.2 | 0.2 | 0.0 | 0.0 |
| Runniness measured after 4-week storage at 60° C. (mm) | | 0.5 | 0.5 | 0.5 | 0.5 | 0.9 | 0.9 | 0.7 | 0.7 | 1.3 | 1.3 | 0.2 | 0.2 | 1.0 | 1.0 | 1.6 | 1.6 |
| Difference between runniness measured just after preparation and runniness measured after 4-week storage at 60° C. (mm) | | 0.5 | 0.5 | 0.5 | 0.5 | 0.9 | 0.9 | 0.7 | 0.7 | 1.2 | 1.2 | 0.2 | 0.2 | 0.8 | 0.8 | 1.6 | 1.6 |

TABLE 2

| Component (parts by mass) | | Example 9 A | Example 9 B | Example 10 A | Example 10 B | Example 11 A | Example 11 B | Example 12 A | Example 12 B | Example 13 A | Example 13 B | Example 14 A | Example 14 B | Example 15 A | Example 15 B | Example 16 A | Example 16 B |
|---|---|---|---|---|---|---|---|---|---|---|---|---|---|---|---|---|---|
| Acid group-containing (meth)acrylic polymerizable monomer (a) | MDP | 5 | | 10 | | 10 | | 10 | | 10 | | 10 | | 10 | | 10 | |
| | 4-META | | 10 | | 10 | | 10 | | 10 | | 10 | | 10 | | 10 | | 10 |
| Polyfunctional (meth)acrylic polymerizable monomer (b) containing no acid group | Bis-GMA | 25 | 70 | 25 | 70 | 25 | 70 | 25 | 70 | 25 | 70 | 25 | 70 | 25 | 70 | 25 | 70 |
| | D-2.6E | 35 | 20 | 35 | 20 | 35 | 20 | 35 | 20 | 35 | 20 | 35 | 20 | 35 | 20 | 35 | 20 |
| | TEGDMA | 35 | | 25 | | 15 | | 20 | | 20 | | 18 | | 30 | | 30 | |
| Amide proton-containing polyfunctional (meth)acrylamide polymerizable monomer (h) | MAEA | | | | | | | | | 10 | | 10 | | | | | |
| | TAC4 | | | | | | | | | | | 2 | | | | | |
| Hydrophilic monofunctional polymerizable monomer (i) | DEAA | | | | | | | 10 | | | | | | | | | |
| | HEMA | | | 5 | | 15 | | | | | | | | | | | |
| Chemical polymerization initiator (c-1) | THP | 3 | | 3 | | 3 | | 3 | | 3 | | 3 | | 3 | | 3 | |
| | BPO | | 1 | | 1 | | 1 | | 1 | | 1 | | 1 | | | | |
| Chemical polymerization initiator (c-2) | DMETU | | | | | | | | | | | | | | 0.5 | | 0.5 |
| | TMTU | | | | | | | | | | | | | 0.1 | | | |
| | DEPT | | | | | | | | | | | | | | | | |
| Photopolymerization initiator (f) | CQ | 0.1 | | 0.1 | | 0.1 | | 0.1 | | 0.1 | | 0.1 | | 0.1 | | 0.1 | |
| Polymerization accelerator (g) | DABE | | 0.1 | | 0.1 | | 0.1 | | 0.1 | | 0.1 | | 0.1 | | 0.1 | | 0.1 |
| | TPBSS | | | | | | | | | | | | | | 2 | | 2 |
| | Na$_2$SO$_3$ | | | | | | | | | | | | | | | | |
| Polymerization inhibitor | BHT | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 |
| Filler (d) | Filler (d-1) | 140 | 140 | 140 | 140 | 140 | 140 | 140 | 140 | 140 | 140 | 140 | 140 | 140 | 140 | 140 | 140 |
| | Filler (d-2) | | | | | | | | | | | | | | | | |
| Filler (e) | Surface-treated silica | | | | | | | | | | | | | | | | |
| | Surface-treated Ba glass powder | 45 | 45 | 45 | 45 | 45 | 45 | 45 | 45 | 45 | 45 | 45 | 45 | 45 | 45 | 45 | 45 |
| | SiO$_2$-coated YBF | | | | | | | | | | | | | | | | |
| | Spherical nanosilica | | | | | | | | | | | | | | | | |
| | Fumed silica | | | | | | | | | | | | | | | | |
| Consistency measured just after preparation (mm) | | 29.9 | 30.7 | 32.3 | 31.5 | 32.0 | 31.9 | 27.0 | 27.2 | | | | | | | | |
| Consistency measured after 4-week storage at 60° C. (mm) | | 31.5 | 31.2 | 33.0 | 32.1 | 33.2 | 32.4 | 28.7 | 28.3 | | | | | | | | |
| Difference between consistency measured just after preparation and consistency measured after 4-week storage at 60° C. (mm) | | 1.6 | 0.5 | 0.7 | 0.6 | 1.2 | 0.5 | 1.7 | 1.1 | | | | | | | | |
| Discharging properties of paste measured just after preparation (N) | | 30.3 | 33.5 | 31.9 | 31.8 | 31.4 | 32.2 | 31.4 | 29.9 | | | | | | | | |
| Discharging properties of paste measured after 4-week storage at 60° C. (N) | | 32.8 | 34.4 | 34.1 | 33.1 | 34.2 | 34.0 | 33.7 | 31.5 | | | | | | | | |
| Difference between discharging properties of paste measured just after preparation and discharging properties of paste measured after 4-week storage at 60° C. (N) | | 2.5 | 0.9 | 2.2 | 1.3 | 2.8 | 1.8 | 2.3 | 1.6 | | | | | | | | |
| Runniness measured just after preparation (mm) | | 0.0 | 0.4 | 0.6 | 0.2 | 0.2 | 0.3 | 0.0 | 0.0 | | | | | | | | |
| Runniness measured after 4-week storage at 60° C. (mm) | | 1.4 | 1.5 | 1.7 | 1.4 | 1.5 | 1.2 | 0.6 | 0.5 | | | | | | | | |
| Difference between runniness measured just after preparation and runniness measured after 4-week storage at 60° C. (mm) | | 1.4 | 1.1 | 1.1 | 1.2 | 1.3 | 0.9 | 0.6 | 0.5 | | | | | | | | |

Note: Due to the dense tabular layout, numerical values for Examples 11–16 are arranged as follows (Consistency / Consistency 4wk / Diff; Discharging / Discharging 4wk / Diff; Runniness / Runniness 4wk / Diff):

- Example 11 A: 32.3, 33.0, 0.7; 31.9, 34.1, 2.2; 0.6, 1.7, 1.1
- Example 11 B: 32.3, 33.0, 0.7 (shared with A column as shown); 31.9, 34.1, 2.2; 0.6, 1.7, 1.1
- Example 12 A: 31.5, 32.1, 0.6; 31.8, 33.1, 1.3; 0.2, 1.4, 1.2
- Example 13 A: 32.0, 33.2, 1.2; 31.4, 34.2, 2.8; 0.2, 1.5, 1.3
- Example 14 A: 31.9, 32.4, 0.5; 32.2, 34.0, 1.8; 0.3, 1.2, 0.9
- Example 15 A: 27.0, 28.7, 1.7; 31.4, 33.7, 2.3; 0.0, 0.6, 0.6
- Example 16 A: 27.2, 28.3, 1.1; 29.9, 31.5, 1.6; 0.0, 0.5, 0.5

As shown in Tables 1 and 2, the dental cements (Examples 1 to 16) according to the present invention show little change in consistency; that is, the difference between the consistency measured just after the preparation and the consistency measured after the 4-week storage at 60° C. is 2 mm or less. Moreover, in the difference between the discharge force measured just after the preparation and the discharge force measured after the 4-week storage at 60° C., little change, namely 3 N or less, is observed. Furthermore, in the difference between the runniness measured just after the preparation and the runniness measured after the 4-week storage at 60° C., little change, namely 2 mm or less, is observed.

TABLE 3

| Component (parts by mass) | | Comparative Example 1 A | Comparative Example 1 B | Comparative Example 2 A | Comparative Example 2 B | Comparative Example 3 A | Comparative Example 3 B | Comparative Example 4 A | Comparative Example 4 B | Comparative Example 5 A | Comparative Example 5 B | Comparative Example 6 A | Comparative Example 6 B |
|---|---|---|---|---|---|---|---|---|---|---|---|---|---|
| Acid group-containing (meth)acrylic polymerizable monomer (a) | MDP | 15 | | 10 | | 10 | | 10 | | 10 | | 10 | |
| | 4-META | | | | | | | | | | | | |
| Polyfunctional (meth)acrylic polymerizable monomer (b) containing no acid group | Bis-GMA | | 15 | 25 | 10 | 25 | 10 | 25 | 10 | 25 | 10 | 25 | 10 |
| | D-2.6E | | | 35 | 70 | 35 | 70 | 35 | 70 | 35 | 70 | 35 | 70 |
| | TEGDMA | | | 30 | 20 | 30 | 20 | 30 | 20 | 30 | 20 | 30 | 20 |
| Amide proton-containing polyfunctional (meth)acrylamide polymerizable monomer (h) | MAEA | | | | | | | | | | | | |
| | TAC4 | | | | | | | | | | | | |
| | DEAA | | | | | | | | | | | | |
| Hydrophilic monofunctional polymerizable monomer (i) | HEMA | 35 | 35 | | | | | | | | | | |
| | THP | 1.5 | | | | | | | | | | | |
| Chemical polymerization initiator (c-1) | BPO | | 3 | | | | | | | | | | |
| Chemical polymerization initiator (c-2) | DMETU | | | 3 | | 3 | | 3 | | 3 | | 3 | |
| | TMTU | | | | 1 | | 1 | | 1 | | 1 | | 1 |
| | DEPT | | | | | | | | | | | | |
| Photopolymerization initiator (f) | CQ | | | 0.1 | | 0.1 | | 0.1 | | 0.1 | | 0.1 | |
| Polymerization accelerator (g) | DABE | | | | | | | | | | | | |
| | TPBSS | | | | | | | | | | | | |
| | Na₂SO₃ | | | | | | | | | | | | |
| Polymerization inhibitor | BHT | 0.1 | 0.025 | 0.1 | 0.1 | 0.1 | 0.1 | 0.1 | 0.1 | 0.1 | 0.1 | 0.1 | 0.1 |
| Filler (d) | Filler (d-1) | | | | | | | | | | | | |
| | Filler (d-2) | | | | | | | | | | | | |
| Filler (e) | Surface-treated silica | 25 | 25 | | | | | | | | | | |
| | Surface-treated Ba glass powder | 95 | 95 | 185 | 140 | 140 | 140 | 140 | 140 | 140 | 140 | 140 | 140 |
| | SiO₂-coated YBF | | | | 45 | 45 | 45 | 45 | 45 | 45 | 45 | 45 | 45 |
| | Spherical nanosilica | | | | | | | | | | | | |
| | Fumed silica | | | | | | | | | | | | |
| Consistency measured just after preparation (mm) | | 35.0 | | 33.2 | | 32.1 | | 30.5 | | 31.7 | | 30.5 | |
| Consistency measured after 4-week storage at 60° C. (mm) | | 61.0 | | Paste A solidified | | Paste A solidified | | Paste A solidified | | Paste A solidified | | 52.8 | |
| Difference between consistency just after preparation and consistency measured after 4-week storage at 60° C. (mm) | | 26.0 | | — | | — | | — | | — | | 22.3 | |
| Discharging properties of paste measured just after preparation (N) | | 42.0 | | 30.9 | | 31.6 | | 33.6 | | 32.4 | | 33.6 | |
| Discharging properties of paste measured after 4-week storage at 60° C. (N) | | 73.0 | | Paste A solidified | | Paste A solidified | | Paste A solidified | | Paste A solidified | | 61.6 | |
| Difference between discharging properties of paste measured just after preparation and discharging properties of paste measured after 4-week storage at 60° C. (N) | | 31.0 | | — | | — | | — | | — | | 28.0 | |
| Runniness measured just after preparation (mm) | | 2.0 | | 0.5 | | 0.3 | | 0.7 | | 0.7 | | 0.7 | |
| Runniness measured after 4-week storage at 60° C. (mm) | | 7.8 | | Paste A solidified | | Paste A solidified | | Paste A solidified | | Paste A solidified | | 6.0 | |
| Difference between runniness measured just after preparation and runniness measured after 4-week storage at 60° C. (mm) | | 5.8 | | — | | — | | — | | — | | 5.3 | |

As shown in Table 3, the dental cements of Comparative Examples 2, 3, 4, and 5 containing no filler (d) of the present invention and employing the silica particles surface-treated with the silane coupling agent (A) alone were solidified after the 4-week storage at 60° C.

The dental cements of Comparative Examples 1 and 6 containing no filler (d) of the present invention and employing the barium glass powder surface-treated with the silane coupling agent (A) alone underwent a significant change in consistency, discharging properties, and runniness after the 4-week storage at 60° C.

INDUSTRIAL APPLICABILITY

The dental cement of the present invention can be suitably used, for example, for luting dental prostheses such as crowns, inlays, and bridges to tooth structures during dental treatment.

The invention claimed is:

1. A multi-part dental cement comprising a first paste and a second paste, wherein
the first paste comprises an acid group-containing (meth)acrylic polymerizable monomer (a), a polyfunctional (meth)acrylic polymerizable monomer (b) containing no acid group, an oxidizing agent (c-1) of a chemical polymerization initiator, and a filler (d),
the second paste comprises a polyfunctional (meth)acrylic polymerizable monomer (b) containing no acid group, a reducing agent (c-2) of a chemical polymerization initiator, and a filler (e),
the acid group-containing (meth)acrylic polymerizable monomer (a) comprises at least one selected from the group consisting of Phosphoric acid group-containing (meth)acrylic polymerizable monomer, pyrophosphoric acid group-containing (meth)acrylic polymerizable monomer, and carboxylic acid group-containing (meth)acrylic polymerizable monomer,
the oxidizing agent (c-1) comprises at least one selected from the group consisting of organic peroxides, azo compounds, and inorganic peroxides,
the reducing agent (c-2) comprises at least one selected from the group consisting of aromatic amines without an electron withdrawing group in the aromatic ring, thiourea compounds, and ascorbic acids,
the filler (d) is treated with a surface treatment agent and has an average particle diameter of 0.03 to 20.0 μm,
the surface treatment agent comprises
a silane coupling agent (A) represented by formula (1):

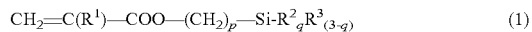

where $R^1$ is a hydrogen atom or a methyl group, $R^2$ is an unsubstituted hydrolyzable group, $R^3$ is an unsubstituted $C_1$ to $C_3$ alkyl group, p is an integer of 1 to 13, and q is 2 or 3, and
an organosilazane (B) represented by formula (2):

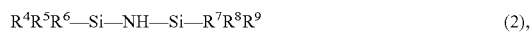

where $R^4$, $R^5$, and $R^6$ are each independently a hydrogen atom or an unsubstituted $C_1$ to $C_3$ alkyl group, at least one of $R^4$, $R^5$, and $R^6$ is an unsubstituted $C_1$ to $C_3$ alkyl group, $R^7$, $R^8$, and $R^9$ are each independently a hydrogen atom or an unsubstituted $C_1$ to $C_3$ alkyl group, and at least one of $R^7$, $R^8$, and $R^9$ is an unsubstituted $C_1$ to $C_3$ alkyl group,
the filler (e) as an average particle diameter of 0.01 to 50.0 μm, and
a molar ratio of the silane coupling agent (A) to the organosilazane (B) represented by [silane coupling agent (A)]:[organosilazane (B)] ranges from 1:1 to 1:20.

2. The multi-part dental cement according to claim 1, wherein the tiller (e) is at least not surface-treated with the organosilazane (B).

3. The multi-part dental cement according to claim 1, wherein the filler (e is surface-treated at least with the organosilazane (B).

4. The multi-part dental cement according to claim 1, wherein $R^2$ is an unsubstituted linear or branched $C_1$ to $C_6$ alkoxy group.

5. The multi-part dental cement according to claim 1, wherein $R^1$ is a methyl group.

6. The multi-part dental cement according to claim 1, wherein p is 2 to 10.

7. The multi-part dental cement according to claim 1, wherein q is 3.

8. The multi-part dental cement according to claim 1, wherein the silane coupling agent (A) is at least one selected front the group consisting of 2-methacryloyloxyethyltrimethoxysilane, 3-methacryloyloxypropyltrimethoxysilane, 4-methacryloyloxybutyltrimethoxysilane, 5-methacryloyloxypentyltrimethoxysilane, and 6-methacryloyloxyhexytrimethoxysilane.

9. The multi-part dental cement according to claim 1, wherein the organosilazane (B) is at least one selected from the group consisting of 1,1,3,3-tetramethyldisilane, 1,1,1,3,3,3-hexamethyldisilazane, and 1,1,1,3,3-pentamethyldisilazane.

10. The multi-part dental cement according to claim 1, wherein
with respect to 100 parts by mass of a total polymerizable monomer components in the first paste, a content of the acid group-containing (meth)acrylic polymerizable monomer is 1 to 50 parts by mass and a content of the filler (d) is 1 to 200 parts by mass, and
with respect to 100 parts by mass of a total polymerizable monomer components in a mixture of the first paste and the second paste, a content of the polyfunctional (meth)acrylic polymerizable monomer (b) containing no acid group is 30 to 95 parts by mass.

11. The multi-part dental cement according to claim 1, wherein at least one of the first paste and the second paste further comprises a photopolymerization initiator (f).

12. The multi-part dental cement according to claim 1, wherein at least one of the first paste and the second paste further comprises an amide proton-containing polyfunctional (meth)acrylamide polymerizable monomer (h).

13. The multi-part dental cement according to claim 12, wherein a content of the amide proton-containing polyfunctional (meth)acrylamide polymerizable monomer (h) is 0.1 to 30 parts by mass with respect to 100 parts by mass of a total polymerizable monomer components in the at least one of the first paste and the second paste.

14. The multi-part dental cement according to claim 1, wherein at least one of the first paste and the second paste further comprises a hydrophilic monofunctional polymerizable monomer (i).

15. The multi-part dental cement according to claim 14, wherein the hydrophilic monofunctional polymerizable monomer (i) is at least one selected from the group consisting of a hydrophilic monofunctional (meth)acrylate polymerizable monomer and a hydrophilic monofunctional (meth)acrylamide polymerizable monomer.

16. The multi-part dental cement according to claim 1, wherein at least one of the first paste and the second paste further comprises a polymerization accelerator (g).

* * * * *